United States Patent
Ludwig

(10) Patent No.: US 7,968,093 B2
(45) Date of Patent: *Jun. 28, 2011

(54) FULLY HUMAN ANTIBODIES DIRECTED AGAINST THE HUMAN INSULIN-LIKE GROWTH FACTOR-1 RECEPTOR

(75) Inventor: Dale L Ludwig, Randolph, NJ (US)

(73) Assignee: ImClone LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/640,671

(22) Filed: Dec. 17, 2009

(65) Prior Publication Data

US 2010/0158920 A1    Jun. 24, 2010

Related U.S. Application Data

(63) Continuation of application No. 10/555,407, filed as application No. PCT/US2004/013852 on May 3, 2004, now Pat. No. 7,638,605.

(60) Provisional application No. 60/467,177, filed on May 1, 2003.

(51) Int. Cl.
| A61K 39/395 | (2006.01) |
| C12P 21/04 | (2006.01) |
| C12P 21/08 | (2006.01) |
| C12N 5/06 | (2006.01) |
| C12N 15/02 | (2006.01) |
| C07K 16/00 | (2006.01) |

(52) U.S. Cl. ............... 424/143.1; 424/141.1; 424/142.1; 424/155.1; 424/181.1; 424/183.1; 435/69.6; 435/70.21; 435/330; 435/449; 530/388.1; 530/388.15; 530/388.22; 530/388.8; 530/391.7

(58) Field of Classification Search .................. None
See application file for complete search history.

(56) References Cited

U.S. PATENT DOCUMENTS

| 4,774,321 A | 9/1988 | Rosner et al. |
| 5,200,509 A | 4/1993 | Spencer et al. |
| 5,262,308 A | 11/1993 | Baserga |
| 5,597,563 A | 1/1997 | Beschorner |
| 5,624,805 A | 4/1997 | Spencer et al. |
| 5,670,341 A | 9/1997 | Spencer et al. |
| 5,681,818 A | 10/1997 | Spencer et al. |
| 5,688,505 A | 11/1997 | Webb et al. |
| 5,705,157 A | 1/1998 | Greene |
| 5,798,266 A | 8/1998 | Quay et al. |
| 5,977,307 A | 11/1999 | Friden et al. |
| 6,316,462 B1 | 11/2001 | Bishop et al. |
| 6,368,826 B1 | 4/2002 | Ligensa et al. |
| 6,875,741 B2 | 4/2005 | Pillutla et al. |
| 7,037,498 B2 | 5/2006 | Cohen et al. |
| 7,071,160 B2 | 7/2006 | Yamano et al. |
| 7,071,300 B2 | 7/2006 | Deshayes et al. |
| 7,217,796 B2 | 5/2007 | Wang et al. |
| 7,241,444 B2 | 7/2007 | Goetsch et al. |
| 7,300,655 B2 | 11/2007 | Hansen et al. |
| 7,329,745 B2 | 2/2008 | Fujita-Yamaguchi |
| 7,371,378 B2 | 5/2008 | Cohen et al. |
| 7,432,244 B2 | 10/2008 | Deshayes et al. |
| 2003/0021780 A1 | 1/2003 | Smith et al. |
| 2003/0165502 A1 | 9/2003 | Fujita-Yamaguchi |
| 2003/0235582 A1 | 12/2003 | Singh et al. |
| 2004/0057950 A1 | 3/2004 | Waksal et al. |
| 2004/0102360 A1 | 5/2004 | Barnett et al. |
| 2004/0116330 A1 | 6/2004 | Naito et al. |
| 2004/0141958 A1 | 7/2004 | Steinaa et al. |
| 2004/0202651 A1 | 10/2004 | Cohen et al. |
| 2004/0202655 A1 | 10/2004 | Morton et al. |
| 2004/0228859 A1 | 11/2004 | Graus et al. |
| 2004/0265307 A1 | 12/2004 | Singh et al. |
| 2005/0008642 A1 | 1/2005 | Graus et al. |
| 2005/0079184 A1 | 4/2005 | Hsing-Chang et al. |
| 2005/0084906 A1 | 4/2005 | Goetsch et al. |
| 2005/0136063 A1 | 6/2005 | Wang et al. |
| 2005/0186203 A1 | 8/2005 | Singh et al. |
| 2005/0244408 A1 | 11/2005 | Cohen et al. |
| 2005/0249728 A1 | 11/2005 | Singh et al. |
| 2005/0249730 A1 | 11/2005 | Goetsch et al. |
| 2005/0281812 A1 | 12/2005 | Cohen et al. |
| 2006/0106203 A1 | 5/2006 | Winter et al. |
| 2006/0134172 A1 | 6/2006 | Shepard et al. |
| 2006/0149033 A1 | 7/2006 | Deshayes et al. |
| 2006/0193772 A1 | 8/2006 | Ochiai et al. |
| 2006/0233814 A1 | 10/2006 | Goldmakher et al. |
| 2007/0009970 A1 | 1/2007 | Heller et al. |
| 2007/0196376 A1 | 8/2007 | Raeber et al. |

FOREIGN PATENT DOCUMENTS

| EP | 0294021 | 12/1988 |
| EP | 0369943 | 5/1990 |
| EP | 0375438 | 6/1990 |
| WO | 8906692 | 7/1989 |
| WO | 96/33735 | 10/1996 |

(Continued)

OTHER PUBLICATIONS

Burtrum, et al., Cancer Research 63(24):8912-8921 (2003).
Hailey, et al., Molecular Cancer Therapeutics, American Association of Cancer Research 1(14):1349-1353 (2002).
Lu, et al., Journal of Biological Chemistry 279(4):2856-2865 (2004).
Vaughan, et al., Nature Biotechnology 14:309-314 (1996).

*Primary Examiner* — David J. Blanchard
(74) *Attorney, Agent, or Firm* — Nicole S. Woods; Sanjay Jivraj

(57) ABSTRACT

This invention relates to human antibodies that bind to human insulin-like growth factor-1 receptor (IGF-IR), to derivatives of these antibodies (Fabs, single chain antibodies, bi-specific antibodies, or fusion proteins), and to uses of the antibodies and derivatives in therapeutic, and diagnostic methods. The invention relates to nucleic acids encoding the anti-IGF-IR, methods of generating the antibodies and expression. The invention further relates to combination therapies using ant-IGF-IR antibodies with anti-neoplastic drugs.

14 Claims, 32 Drawing Sheets

FOREIGN PATENT DOCUMENTS

| | | |
|---|---|---|
| WO | 9744352 | 11/1997 |
| WO | 02053596 | 7/2002 |
| WO | 03059951 | 7/2003 |
| WO | 03/100008 | 12/2003 |
| WO | 2004071529 | 8/2004 |
| WO | 2004083248 | 9/2004 |
| WO | 2004087756 | 10/2004 |
| WO | 2005005635 | 1/2005 |
| WO | 2005052005 | 6/2005 |
| WO | 2005082415 | 9/2005 |
| WO | 2006008639 | 1/2006 |
| WO | 2006013472 | 2/2006 |
| WO | 2006060419 | 6/2006 |
| WO | 2006069202 | 6/2006 |
| WO | 2007000328 | 1/2007 |
| WO | 2007012614 | 2/2007 |
| WO | 2007031875 | 3/2007 |

Figure 1

| | |
|---|---|
| GAGGTCCAGCTGGTGCAGTCTGGGGCTGAGGTGAAGAAGCCTGGGTCCTC | 50 |
| GGTGAAGGTCTCCTGCAAGGCTTCTGGAGGCACCTTCAGCAGCTATGCTA | 100 |
| TCAGCTGGGTGCGACAGGCCCCTGGACAAGGGCTTGAGTGGATGGGAGGG | 150 |
| ATCATCCCTATCTTTGGTACAGCAAACTACGCACAGAAGTTCCAGGGCAG | 200 |
| AGTCACGATTACCGCGGACAAATCCACGAGCACAGCCTACATGGAGCTGA | 250 |
| GCAGCCTGAGATCTGAGGACACGGCCGTGTATTACTGTGCGAGAGCGCCA | 300 |
| TTACGATTTTTGGAGTGGTCCACCCAAGACCACTACTACTACTACTACAT | 350 |
| GGACGTCTGGGGCAAAGGGACCACGGTCACCGTCTCAAGC | 390 |

Figure 2

```
EVQLVQSGAEVKKPGSSVKVSCKASGGTFSSYAISWVRQAPGQGLEWMGG      50
IIPIFGTANYAQKFQGRVTITADKSTSTAYMELSSLRSEDTAVYYCARAP     100
LRFLEWSTQDHYYYYYMDVWGKGTTVTVSS                         130
```

Figure 3

| | |
|---|---|
| ATGGGATGGTCATGTATCATCCTTTTTTCTAGTAGCAACTGCAACTGGAGT | 50 |
| ACATTCAGAGGTCCAGCTGGTGCAGTCTGGGGCTGAGGTGAAGAAGCCTG | 100 |
| GGTCCTCGGTGAAGGTCTCCTGCAAGGCTTCTGGAGGCACCTTCAGCAGC | 150 |
| TATGCTATCAGCTGGGTGCGACAGGCCCCTGGACAAGGGCTTGAGTGGAT | 200 |
| GGGAGGGATCATCCCTATCTTTGGTACAGCAAACTACGCACAGAAGTTCC | 250 |
| AGGGCAGAGTCACGATTACCGCGGACAAATCCACGAGCACAGCCTACATG | 300 |
| GAGCTGAGCAGCCTGAGATCTGAGGACACGGCCGTGTATTACTGTGCGAG | 350 |
| AGCGCCATTACGATTTTTGGAGTGGTCCACCCAAGACCACTACTACTACT | 400 |
| ACTACATGGACGTCTGGGGCAAAGGGACCACGGTCACCGTCTCAAGCGCC | 450 |
| TCCACCAAGGGCCCATCGGTCTTCCCCCTGGCACCCTCCTCCAAGAGCAC | 500 |
| CTCTGGGGGCACAGCGGCCCTGGGCTGCCTGGTCAAGGACTACTTCCCCG | 550 |
| AACCGGTGACGGTGTCGTGGAACTCAGGCGCCCTGACCAGCGGCGTGCAC | 600 |
| ACCTTCCCGGCTGTCCTACAGTCCTCAGGACTCTACTCCCTCAGCAGCGT | 650 |
| GGTGACCGTGCCCTCCAGCAGCTTGGGCACCCAGACCTACATCTGCAACG | 700 |
| TGAATCACAAGCCCAGCAACACCAAGGTGGACAAGAAAGTTGAGCCCAAA | 750 |
| TCTTGTGACAAAACTCACACATGCCCACCGTGCCCAGCACCTGAACTCCT | 800 |
| GGGGGGACCGTCAGTCTTCCTCTTCCCCCCAAAACCCAAGGACACCCTCA | 850 |
| TGATCTCCCGGACCCCTGAGGTCACATGCGTGGTGGTGGACGTGAGCCAC | 900 |
| GAAGACCCTGAGGTCAAGTTCAACTGGTACGTGGACGGCGTGGAGGTGCA | 950 |
| TAATGCCAAGACAAAGCCGCGGGAGGAGCAGTACAACAGCACGTACCGGG | 1000 |
| TGGTCAGCGTCCTCACCGTCCTGCACCAGGACTGGCTGAATGGCAAGGAG | 1050 |
| TACAAGTGCAAGGTCTCCAACAAAGCCCTCCCAGCCCCCATCGAGAAAAC | 1100 |
| CATCTCCAAAGCCAAAGGGCAGCCCCGAGAACCACAGGTGTACACCCTGC | 1150 |
| CCCCATCCCGGGAGGAGATGACCAAGAACCAGGTCAGCCTGACCTGCCTG | 1200 |
| GTCAAAGGCTTCTATCCCAGCGACATCGCCGTGGAGTGGGAGAGCAATGG | 1250 |
| GCAGCCGGAGAACAACTACAAGACCACGCCTCCCGTGCTGGACTCCGACG | 1300 |
| GCTCCTTCTTCCTCTACAGCAAGCTCACCGTGGACAAGAGCAGGTGGCAG | 1350 |
| CAGGGGAACGTCTTCTCATGCTCCGTGATGCATGAGGCTCTGCACAACCA | 1400 |
| CTACACGCAGAAGAGCCTCTCCCTGTCTCCGGGTAAATGA | 1440 |

Figure 4

| | |
|---|---|
| MGWSCIILFLVATATGVHSEVQLVQSGAEVKKPGSSVKVSCKASGGTFSS | 50 |
| YAISWVRQAPGQGLEWMGGIIPIFGTANYAQKFQGRVTITADKSTSTAYM | 100 |
| ELSSLRSEDTAVYYCARAPLRFLEWSTQDHYYYYYMDVWGKGTTVTVSSA | 150 |
| STKGPSVFPLAPSSKSTSGGTAALGCLVKDYFPEPVTVSWNSGALTSGVH | 200 |
| TFPAVLQSSGLYSLSSVVTVPSSSLGTQTYICNVNHKPSNTKVDKKVEPK | 250 |
| SCDKTHTCPPCPAPELLGGPSVFLFPPKPKDTLMISRTPEVTCVVVDVSH | 300 |
| EDPEVKFNWYVDGVEVHNAKTKPREEQYNSTYRVVSVLTVLHQDWLNGKE | 350 |
| YKCKVSNKALPAPIEKTISKAKGQPREPQVYTLPPSREEMTKNQVSLTCL | 400 |
| VKGFYPSDIAVEWESNGQPENNYKTTPPVLDSDGSFFLYSKLTVDKSRWQ | 450 |
| QGNVFSCSVMHEALHNHYTQKSLSLSPGK | 479 |

Figure 5

```
TCTTCTGAGCTGACTCAGGACCCTGCTGTGTCTGTGGCCTTGGGACAGAC        50
AGTCAGGATCACATGCCAAGGAGACAGCCTCAGAAGCTATTATGCAAGCT       100
GGTACCAGCAGAAGCCAGGACAGGCCCCTGTACTTGTCATCTATGGTAAA       150
AACAACCGGCCCTCAGGGATCCCAGACCGATTCTCTGGCTCCAGCTCAGG       200
AAACACAGCTTCCTTGACCATCACTGGGCTCAGGCGGAAGATGAGGCTG        250
ACTATTACTGTAACTCCCGGGACAACAGTGATAACCGTCTGATATTTGGC       300
GGCGGGACCAAGCTGACCGTCCTCAGT                              327
```

Figure 6

SSELTQDPAVSVALGQTVRITC<u>QGDSLRSYYAS</u>WYQQKPGQAPVLVIY<u>GK 50
NNRPS</u>GIPDRFSGSSSGNTASLTITGAQAEDEADYYC<u>NSRDNSDNRLI</u>FG 100
GGTKLTVLS 109

Figure 7

| | |
|---|---|
| ATGGGATGGTCATGTATCATCCTTTTTCTAGTAGCAACTGCAACTGGAGT | 50 |
| ACATTCATCTTCTGAGCTGACTCAGGACCCTGCTGTGTCTGTGGCCTTGG | 100 |
| GACAGACAGTCAGGATCACATGCCAAGGAGACAGCCTCAGAAGCTATTAT | 150 |
| GCAAGCTGGTACCAGCAGAAGCCAGGACAGGCCCCTGTACTTGTCATCTA | 200 |
| TGGTAAAAACAACCGGCCCTCAGGGATCCCAGACCGATTCTCTGGCTCCA | 250 |
| GCTCAGGAAACACAGCTTCCTTGACCATCACTGGGGCTCAGGCGGAAGAT | 300 |
| GAGGCTGACTATTACTGTAACTCCCGGGACAACAGTGATAACCGTCTGAT | 350 |
| ATTTGGCGGCGGGACCAAGCTGACCGTCCTCAGTCAGCCCAAGGCTGCCC | 400 |
| CCTCGGTCACTCTGTTCCCGCCCTCCTCTGAGGAGCTTCAAGCCAACAAG | 450 |
| GCCACACTGGTGTGTCTCATAAGTGACTTCTACCCGGGAGCCGTGACAGT | 500 |
| GGCCTGGAAGGCAGATAGCAGCCCCGTCAAGGCGGGAGTGGAGACCACCA | 550 |
| CACCCTCCAAACAAAGCAACAACAAGTACGCGGCCAGCAGCTATCTGAGC | 600 |
| CTGACGCCTGAGCAGTGGAAGTCCCACAGAAGCTACAGCTGCCAGGTCAC | 650 |
| GCATGAAGGGAGCACCGTGGAGAAGACAGTGGCCCCTGCAGAATGCTCTT | 700 |
| GA | 702 |

Figure 8

```
MGWSCIILFLVATATGVHSSSELTQDPAVSVALGQTVRITCQGDSLRSYY    50
ASWYQQKPGQAPVLVIYGKNNRPSGIPDRFSGSSSGNTASLTITGAQAED   100
EADYYCNSRDNSDNRLIFGGGTKLTVLSQPKAAPSVTLFPPSSEELQANK   150
ATLVCLISDFYPGAVTVAWKADSSPVKAGVETTTPSKQSNNKYAASSYLS   200
LTPEQWKSHRSYSCQVTHEGSTVEKTVAPAECS                    233
```

Figure 9

```
TCTTCTGAGCTGACTCAGGACCCTGCTGTGTCTGTGGCCTTGGGACAGAC         50
AGTCAGGATCACATGCCAAGGAGACAGCCTCAGAAGCTATTATGCAACCT        100
GGTACCAGCAGAAGCCAGGACAGGCCCCTATTCTTGTCATCTATGGTGAA        150
AATAAGCGGCCCTCAGGGATCCCAGACCGATTCTCTGGCTCCAGCTCAGG        200
AAACACAGCTTCCTTGACCATCACTGGGGCTCAGGCAGAAGATGAGGCTG        250
ACTACTATTGTAAATCTCGGGATGGCAGTGGTCAACATCTGGTGTTCGGC        300
GGAGGGACCAAGCTGACCGTCCTAGGT                               327
```

Figure 10

```
SSELTQDPAVSVALGQTVRITCQGDSLRSYYATWYQQKPGQAPILVIYGE          50
NKRPSGIPDRFSGSSSGNTASLTITGAQAEDEADYYCKSRDGSGQHLVFG         100
GGTKLTVLG                                                  109
```

Figure 11

| | |
|---|---|
| ATGGGATGGTCATGTATCATCCTTTTTCTAGTAGCAACTGCAACTGGAGT | 50 |
| ACATTCATCTTCTGAGCTGACTCAGGACCCTGCTGTGTCTGTGGCCTTGG | 100 |
| GACAGACAGTCAGGATCACATGCCAAGGAGACAGCCTCAGAAGCTATTAT | 150 |
| GCAACCTGGTACCAGCAGAAGCCAGGACAGGCCCCTATTCTTGTCATCTA | 200 |
| TGGTGAAAATAAGCGGCCCTCAGGGATCCCAGACCGATTCTCTGGCTCCA | 250 |
| GCTCAGGAAACACAGCTTCCTTGACCATCACTGGGGCTCAGGCAGAAGAT | 300 |
| GAGGCTGACTACTATTGTAAATCTCGGGATGGCAGTGGTCAACATCTGGT | 350 |
| GTTCGGCGGAGGGACCAAGCTGACCGTCCTAGGTCAGCCCAAGGCTGCCC | 400 |
| CCTCGGTCACTCTGTTCCCGCCCTCCTCTGAGGAGCTTCAAGCCAACAAG | 450 |
| GCCACACTGGTGTGTCTCATAAGTGACTTCTACCCGGGAGCCGTGACAGT | 500 |
| GGCCTGGAAGGCAGATAGCAGCCCCGTCAAGGCGGGAGTGGAGACCACCA | 550 |
| CACCCTCCAAACAAAGCAACAACAAGTACGCGGCCAGCAGCTATCTGAGC | 600 |
| CTGACGCCTGAGCAGTGGAAGTCCCACAGAAGCTACAGCTGCCAGGTCAC | 650 |
| GCATGAAGGGAGCACCGTGGAGAAGACAGTGGCCCCTGCAGAATGCTCTT | 700 |
| GA | 702 |

Figure 12

| | |
|---|---|
| MGWSCIILFLVATATGVHSSSELTQDPAVSVALGQTVRITCQGDSLRSYY | 50 |
| ATWYQQKPGQAPILVIYGENKRPSGIPDRFSGSSSGNTASLTITGAQAED | 100 |
| EADYYCKSRDGSGQHLVFGGGTKLTVLGQPKAAPSVTLFPPSSEELQANK | 150 |
| ATLVCLISDFYPGAVTVAWKADSSPVKAGVETTTPSKQSNNKYAASSYLS | 200 |
| LTPEQWKSHRSYSCQVTHEGSTVEKTVAPAECS | 233 |

Figure 13

Heavy chain
CDR1          CDR2                       CDR3
SYAIS         GIIPIFGTANYAQKFQG          APLRFLEWSTQDHYYYYYMDV         2F8/A12

Light chain
CDR1              CDR2            CDR3
QGDSLRSYYAS       GKNNRPS         NSRDNSDNRLI            2F8
QGDSLRSYYAT       GENKRPS         KSRDGSGQHLV            A12

Figure 14

```
                        10                  20    CDR1    30                40                 50
2F8  S S E L T Q D P A V S V A L G Q T V R I T C Q G D S L R S Y Y A S W Y Q Q K P G Q A P V L V I Y G K
A12  S S E L T Q D P A V S V A L G Q T V R I T C Q G D S L R S Y Y A T W Y Q Q K P G Q A P I L V I Y G E

CDR2            60                  70                  80                  90    CDR3    100
2F8  N N R P S G I P D R F S G S S S G N T A S L T I T G A Q A E D E A D Y Y C N S R D N S D N R L I F G
A12  N K R P S G I P D R F S G S S S G N T A S L T I T G A Q A E D E A D Y Y C K S R D G S G Q H L V F G 109
2F8  G G T K L T V L S
A12  G G T K L T V L G
```

Figure 19A
|  |  |  |  |  |  |  |
|---|---|---|---|---|---|---|
| 10nM IGF I | − | − | − | + | + | + |
| 100nM 2F8 | − | + | − | − | + | − |
| 100nM A12λ | − | − | + | − | − | + |
P-tyrosine
IGF IRβ subunit Figure 20A
| | | | | | | |
|---|---|---|---|---|---|---|
| 10nM IGF I | − | − | − | + | + | + |
| 100nM 2F8 | − | + | − | − | + | − |
| 100nM A12λ | − | − | + | − | − | + |
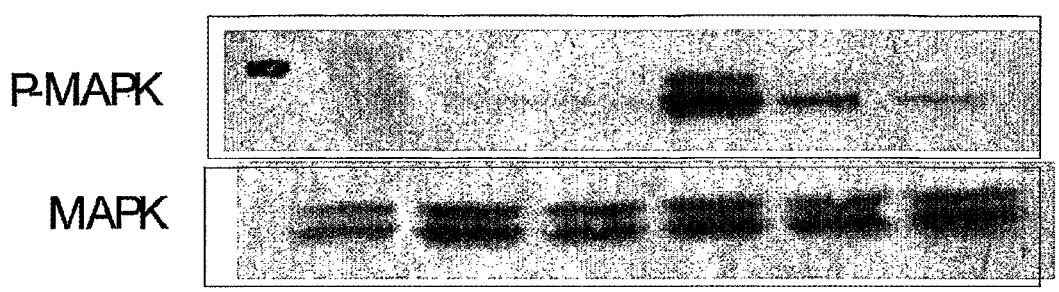
P-MAPK
MAPK
| | | | | Antibody concentration: | 100nM | | 50nM | | 10nM | |
|---|---|---|---|---|---|---|---|---|---|---|
| 10nM IGF I | − | − | − | + | + | + | + | + | + | + |
| Mab − 2F8 | − | − | − | − | + | − | + | − | + | − |
| Mab − A12λ | − | − | − | − | − | + | − | + | − | + |
P-AKT
Figure 20B Figure 21
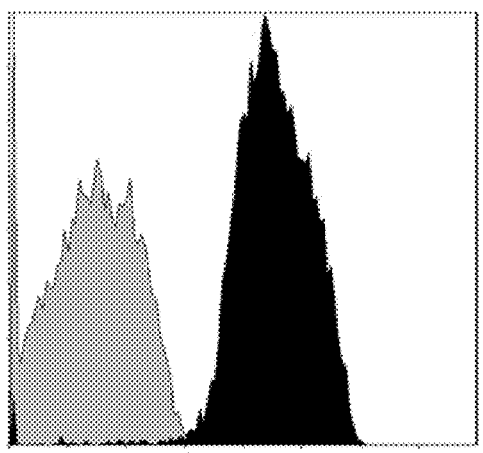
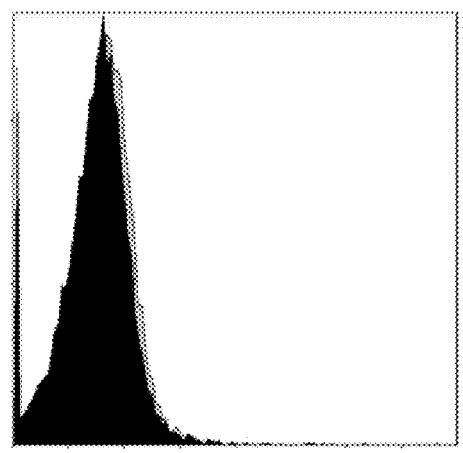
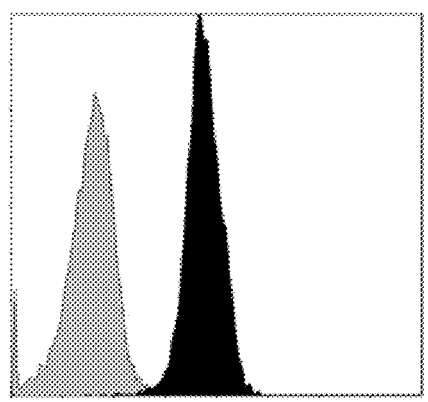
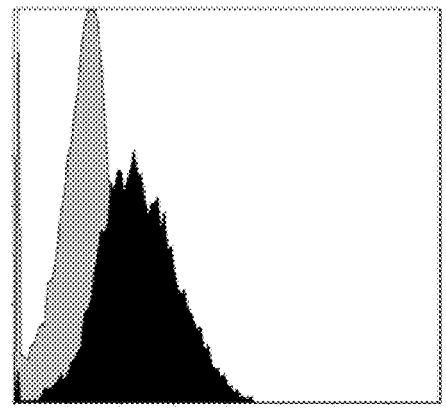

FULLY HUMAN ANTIBODIES DIRECTED AGAINST THE HUMAN INSULIN-LIKE GROWTH FACTOR-1 RECEPTOR

This application is a continuation of U.S. patent application Ser. No. 10/555,407, filed Jun. 8, 2007 now U.S. Pat. No. 7,638,605 which claims priority of and is a U.S. national phase application of PCT/US2004/013852, filed May 3, 2004, which claims priority of U.S. Provisional Application No. 60/467,177, filed May 1, 2003.

BACKGROUND

The insulin-like growth factor receptor (IGF-IR) is a ubiquitous transmembrane tyrosine kinase receptor that is essential for normal fetal and post-natal growth and development. IGF-IR can stimulate cell proliferation, cell differentiation, changes in cell size, and protect cells from apoptosis. It has also been considered to be quasi-obligatory for cell transformation (reviewed in Adams et al., *Cell. Mol. Life Sci.* 57:1050-93 (2000); Baserga, *Oncogene* 19:5574-81 (2000)). The IGF-IR is located on the cell surface of most cell types and serves as the signaling molecule for growth factors IGF-I and IGF-II (collectively termed henceforth IGFs). IGF-IR also binds insulin, albeit at three orders of magnitude lower affinity than it binds to IGFs. IGF-IR is a pre-formed heterotetramer containing two alpha and two beta chains covalently linked by disulfide bonds. The receptor subunits are synthesized as part of a single polypeptide chain of 180 kd, which is then proteolytically processed into alpha (130 kd) and beta (95 kd) subunits. The entire alpha chain is extracellular and contains the site for ligand binding. The beta chain possesses the transmembrane domain, the tyrosine kinase domain, and a C-terminal extension that is necessary for cell differentiation and transformation, but is dispensable for mitogen signaling and protection from apoptosis.

IGF-IR is highly similar to the insulin receptor (IR), particularly within the beta chain sequence (70% homology). Because of this homology, recent studies have demonstrated that these receptors can form hybrids containing one IR dimer and one IGF-IR dimer (Pandini et al., *Clin. Canc. Res.* 5:1935-19 (1999)). The formation of hybrids occurs in both normal and transformed cells and the hybrid content is dependent upon the concentration of the two homodimer receptors (IR and IGF-IR) within the cell. In one study of 39 breast cancer specimens, although both IR and IGF-IR were overexpressed in all tumor samples, hybrid receptor content consistently exceeded the levels of both homo-receptors by approximately 3-fold (Pandini et al., *Clin. Canc. Res.* 5:1935-44 (1999)). Although hybrid receptors are composed of IR and IGF-IR pairs, the hybrids bind selectively to IGFs, with affinity similar to that of IGF-IR, and only weakly bind insulin (Siddle and Soos, The IGF System. Humana Press. pp. 199-225. 1999). These hybrids therefore can bind IGFs and transduce signals in both normal and transformed cells.

A second IGF receptor, IGF-IIR, or mannose-6-phosphate (M6P) receptor, also binds IGF-II ligand with high affinity, but lacks tyrosine kinase activity (Oates et al., *Breast Cancer Res. Treat.* 47:269-81 (1998)). Because it results in the degradation of IGF-II, it is considered a sink for IGF-II, antagonizing the growth promoting effects of this ligand. Loss of the IGF-IIR in tumor cells can enhance growth potential through release of its antagonistic effect on the binding of IGF-II with the IGF-IR (Byrd et al., *J. Biol. Chem.* 274:24408-16 (1999)).

Endocrine expression of IGF-I is regulated primarily by growth hormone and produced in the liver, but recent evidence suggests that many other tissue types are also capable of expressing IGF-I. This ligand is therefore subjected to endocrine and paracrine regulation, as well as autocrine in the case of many types of tumor cells (Yu, H. and Rohan, J., *J. Natl. Cancer Inst.* 92:1472-89 (2000)).

Six IGF binding proteins (IGFBPs) with specific binding affinities for the IGFs have been identified in serum (Yu, H. and Rohan, J., *J. Natl. Cancer Inst.* 92:1472-89 (2000)). IGFBPs can either enhance or inhibit the action of IGFs, as determined by the molecular structures of the binding proteins as a result of post-translational modifications. Their primary roles are for transport of IGFs, protection of IGFs from proteolytic degradation, and regulation of the interaction of IGFs with IGF-IR. Only about 1% of serum IGF-I is present as free ligand, the remainder is associated with IGFBPs (Yu, H. and Rohan, J., *J. Natl. Cancer Inst.* 92:1472-89 (2000)).

Upon binding of ligand (IGFs), the IGF-IR undergoes autophosphorylation at conserved tyrosine residues within the catalytic domain of the beta chain. Subsequent phosphorylation of additional tyrosine residues within the beta chain provides docking sites for the recruitment of downstream molecules critical to the signaling cascade. The principle pathways for transduction of the IGF signal are mitogen activated protein kinase (MAPK) and phosphatidylinositol 3-kinase (PI3K) (reviewed in Blakesley et al., In: The IGF System. Humana Press. 143-163 (1999)). The MAPK pathway is primarily responsible for the mitogenic signal elicited following IGFs stimulation and PI3K is responsible for the IGF-dependent induction of anti-apoptotic or survival processes.

A key role of IGF-IR signaling is its anti-apoptotic or survival function. Activated IGF-IR signals PI3K and downstream phosphorylation of Akt, or protein kinase B. Akt can effectively block, through phosphorylation, molecules such as BAD, which are essential for the initiation of programmed cell death, and inhibit initiation of apoptosis (Datta et al., *Cell* 91:231-41 (1997)). Apoptosis is an important cellular mechanism that is critical to normal developmental processes (Oppenheim, *Annu. Rev. Neurosci.* 14:453-501 (1991)). It is a key mechanism for effecting the elimination of severely damaged cells and reducing the potential persistence of mutagenic lesions that may promote tumorigenesis. To this end, it has been demonstrated that activation of IGFs signaling can promote the formation of spontaneous tumors in a mouse transgenic model (DiGiovanni et al., *Cancer Res.* 60:1561-70 (2000)). Furthermore, IGF over-expression can rescue cells from chemotherapy induced cell death and may be an important factor in tumor cell drug resistance (Gooch et al., *Breast Cancer Res. Treat.* 56:1-10 (1999)). Consequently, modulation of the IGF signaling pathway has been shown to increase the sensitivity of tumor cells to chemotherapeutic agents (Benini et al., *Clinical Cancer Res.* 7:1790-97 (2001)).

A large number of research and clinical studies have implicated the IGF-IR and its ligands (IGFs) in the development, maintenance, and progression of cancer. In tumor cells, over-expression of the receptor, often in concert with over-expression of IGF ligands, leads to potentiation of these signals and, as a result, enhanced cell proliferation and survival. IGF-I and IGF-II have been shown to be strong mitogens for a wide variety of cancer cell lines including prostate (Nickerson et al., *Cancer Res.* 61:6276-80 (2001); Hellawell et al., *Cancer Res.* 62:2942-50 (2002)) breast (Gooch et al., *Breast Cancer Res. Treat.* 56:1-10 (1999)), lung, colon (Hassan and Macaulay, *Ann. Oncol.* 13:349-56 (2002)), stomach, leukemia, pancreas, brain, myeloma (Ge and Rudikoff, *Blood* 96:2856-61 (2000), melanoma (All-Ericsson et al., *Invest. Opthalmol. Vis. Sci.* 43:1-8 (2002)), and ovary (reviewed in:

Macaulay, *Br. J. Cancer* 65:311-20 (1990)) and this effect is mediated through the IGF-IR. High circulating levels of IGF-I in serum have been associated with an increased risk of breast, prostate, and colon cancer (Pollak, *Eur. J. Cancer* 36:1224-28 (2000)). In a mouse model of colon cancer, increases in circulating IGF-I levels in vivo led to a significant increase in the incidence of tumor growth and metastasis (Wu et al., *Cancer Res.* 62: 1030-35 (2002)). Constitutive expression of IGF-I in epidermal basal cells of transgenic mice has been shown to promote spontaneous tumor formation (Di-Giovanni et al., *Cancer Res.* 60:1561-1570 (2000; Bol et al., *Oncogene* 14:1725-1734 (1997)). Over-expression of IGF-II in cell lines and tumors occurs with high frequency and may result from loss of genomic imprinting of the IGF-II gene (Yaginuma et al., *Oncology* 54:502-7 (1997)). Receptor over-expression has been demonstrated in many diverse human tumor types including lung (Quinn et al., *J. Biol. Chem.* 271:11477-83 (1996)), breast (Cullen et al., *Cancer Res.* 50: 48-53 (1990); Peyrat and Bonneterre, *Cancer Res.* 22:59-67 (1992); Lee and Yee, *Biomed. Pharmacother.* 49:415-21 (1995)), sarcoma (van Valen et al., *J. Cancer Res. Clin. Oncol.* 118:269-75 (1992); Scotlandi et al., *Cancer Res.* 56:4570-74 (1996)), prostate (Nickerson et al., *Cancer Res.* 61:6276-80 (2001)), and colon (Hassan and Macaulay, *Ann. Oncol.* 13:349-56 (2002)). In addition, highly metastatic cancer cells have been shown to possess higher expression of IGF-II and IGF-IR than tumor cells that are less prone to metastasize (Guerra et al., *Int. J. Cancer* 65:812-20 (1996)). A critical role of the IGF-IR in cell proliferation and transformation was demonstrated in experiments of IGF-IR knockout derived mouse embryo fibroblasts. These primary cells grow at significantly reduced rates in culture medium containing 10% serum and fail to transform by a variety of oncogenes including SV40 Large T (Sell et al., *Mol. Cell. Biol.* 3604-12 (1994)). Recently it was demonstrated that resistance to the drug Herceptin in some forms of breast cancer may be due to activation of IGF-IR signaling in those cancers (Lu et al., *J. Natl. Cancer Inst.* 93:1852-57 (2001)). Over-expression or activation of IGF-IR may therefore not only be a major determinant in tumorigenicity, but also in tumor cell drug resistance.

Activation of the IGF system has also been implicated in several pathological conditions besides cancer, including acromegaly (Drange and Melmed. In: The IGF System. Humana Press. 699-720 (1999)), retinal neovascularization (Smith et al., *Nature Med.* 12:1390-95 (1999)), and psoriasis (Wraight et al., *Nature Biotech.* 18:521-26 (2000)). In the latter study, an antisense oligonucleotide preparation targeting the IGF-IR was effective in significantly inhibiting the hyperproliferation of epidermal cells in human psoriatic skin grafts in a mouse model, suggesting that anti-IGF-IR therapies may be an effective treatment for this chronic disorder.

A variety of strategies have been developed to inhibit the IGF-IR signaling pathway in cells. Antisense oligonucleotides have been effective in vitro and in experimental mouse models, as shown above for psoriasis. In addition, inhibitory peptides targeting the IGF-IR have been generated that possess anti-proliferative activity in vitro and in vivo (Pietrzkowski et al., *Cancer Res.* 52:6447-51 (1992); Haylor et al., *J. Am. Soc. Nephrol.* 11:2027-35 (2000)). A synthetic peptide sequence from the C-terminus of IGF-IR has been shown to induce apoptosis and significantly inhibit tumor growth (Reiss et al., *J. Cell. Phys.* 181:124-35 (1999)). Several dominant-negative mutants of the IGF-IR have also been generated which, upon over-expression in tumor cell lines, compete with wild-type IGF-IR for ligand and effectively inhibit tumor cell growth in vitro and in vivo (Scotlandi et al., *Int. J. Cancer* 101:11-6 (2002); Seely et al., *BMC Cancer* 2:15 (2002)). Additionally, a soluble form of the IGF-IR has also been demonstrated to inhibit tumor growth in vivo (D'Ambrosio et al., *Cancer Res.* 56:4013-20 (1996)). Antibodies directed against the human IGF-IR have also been shown to inhibit tumor cell proliferation in vitro and tumorigenesis in vivo including cell lines derived from breast cancer (Artega and Osborne, *Cancer Res.* 49:6237-41 (1989)), Ewing's osteosarcoma (Scotlandi et al., *Cancer Res.* 58:4127-31 (1998)), and melanoma (Furlanetto et al., *Cancer Res.* 53:2522-26 (1993)). Antibodies are attractive therapeutics chiefly because of they 1) can possess high selectivity for a particular protein antigen, 2) are capable of exhibiting high affinity binding to the antigen, 3) possess long half-lives in vivo, and, since they are natural immune products, should 4) exhibit low in vivo toxicity (Park and Smolen. In: Advances in Protein Chemistry. Academic Press. pp: 360-421 (2001)). Antibodies derived from non-human sources, e.g.: mouse, may, however, effect a directed immune response against the therapeutic antibody, following repeated application, thereby neutralizing the antibody's effectiveness. Fully human antibodies offer the greatest potential for success as human therapeutics since they would likely be less immunogenic than murine or chimeric antibodies in humans, similar to naturally occurring immuno-responsive antibodies. To this end, there is a need to develop high affinity human anti-IGF-IR monoclonal antibodies for therapeutic use.

SUMMARY OF THE INVENTION

The invention provides human monoclonal antibodies and fragments thereof that bind specifically to the human IGF-I receptor. The antibodies have at least one property selected from (i) inhibits binding of IGF-I or IGF-II to IGF-IR, (ii) neutralizes activation of IGF-IR by IGF-I or IGF-II, (iii) reduces IGF-IR surface receptor by at least about 80%; and (iv) binds to IGF-IR with a Kd of about $3 \times 10^{-10}$ or less. In a more preferred embodiment, an antibody of the invention reduces IGF-IR surface receptor by at least about 85%, and more preferably by at least about 90%. Further, the antibodies inhibit ligand-mediated receptor autophosphorylation and downstream cellular signaling through the MAPK and Akt pathways. Antibodies of the invention, used alone or in combination with an anti-neoplastic agent, are particularly useful for treating neoplastic diseases and hyperproliferative disorders.

The invention provides isolated polynucleotides encoding the antibodies or fragments thereof, expression vectors comprising the polynucleotide sequences, and host cells for expression.

Further, the invention provides pharmaceutical compositions and diagnostic and therapeutic methods for treatment of tumors and hyperproliferative disease. The methods can further comprise administration of an anti-neoplastic agent or treatment.

BRIEF DESCRIPTION OF THE FIGURES

FIG. 1 depicts the nucleotide sequence of the 2F8 heavy chain variable domain (SEQ ID NO:1).

FIG. 2 depicts the amino acid sequence of the 2F8 heavy chain variable domain. CDRs are in bold and underlined (SEQ ID NO:2).

FIG. 3 depicts the nucleotide sequence of the complete 2F8 heavy chain (underline: secretory signal sequence; italics: IgG1 constant region) (SEQ ID NO:3).

FIG. 4 depicts the amino acid sequence of the complete 2F8 heavy chain (underline: secretory signal sequence; bold: CDRs; italics: IgG1 constant region) (SEQ ID NO:4).

FIG. 5 depicts the nucleotide sequence of the 2F8 light chain variable domain (SEQ ID NO:5).

FIG. 6 depicts the amino acid sequence of the 2F8 light chain variable domain. CDRs are in bold and underlined (SEQ ID NO:6).

FIG. 7 depicts the nucleotide sequence of the complete 2F8 light chain (underline: secretory signal sequence; italics: IgG1 constant region) (SEQ ID NO:7).

FIG. 8 depicts the amino acid sequence of the complete 2F8 light chain (underline: secretory signal sequence; bold: CDRs; italics: IgG1 constant region) (SEQ ID NO:8).

FIG. 9 depicts the nucleotide sequence of the A12 light chain variable domain (SEQ ID NO:9).

FIG. 10 depicts the amino acid sequence of the A12 light chain variable domain. CDRs are in bold and underlined (SEQ ID NO:10).

FIG. 11 depicts the nucleotide sequence of the complete A12 light chain (underline: secretory signal sequence; italics: IgG1 constant region) (SEQ ID NO:11).

FIG. 12 depicts the amino acid sequence of the complete A12 light chain (underline: secretory signal sequence; bold: CDRs; italics: IgG1 constant region) (SEQ ID NO:12).

FIG. 13 depicts $V_H$ and $V_L$ CDR sequences of antibodies 2F8 and A12. Differences between the $V_L$ CDRs are underlined.

FIG. 14 depicts the homology between 2F8 and A12 light chain variable region amino acid sequences. Sequences differences are boxed and CDRs are highlighted.

FIG. 18 shows the effect of antibody A12 on $^3$H-thymidine incorporation in a mitogenesis assay.

FIG. 20 shows inhibition of IGF-I mediated phosphorylation of downstream effector molecules by antibodies A12 and 2F8. Panel A: inhibition of phosphorylation of MAPK; Panel B: inhibition of phosphorylation of Akt.

FIG. 21 shows binding of antibody A12 to human and murine IGF-IR positive and negative cell lines. MCF7: human breast cancer cells; R—: mouse embryo fibroblasts; HEL: human leukemia cells; Lewis Lung: mouse lung carcinoma cells.

DETAILED DESCRIPTION OF THE INVENTION

Figure 15:
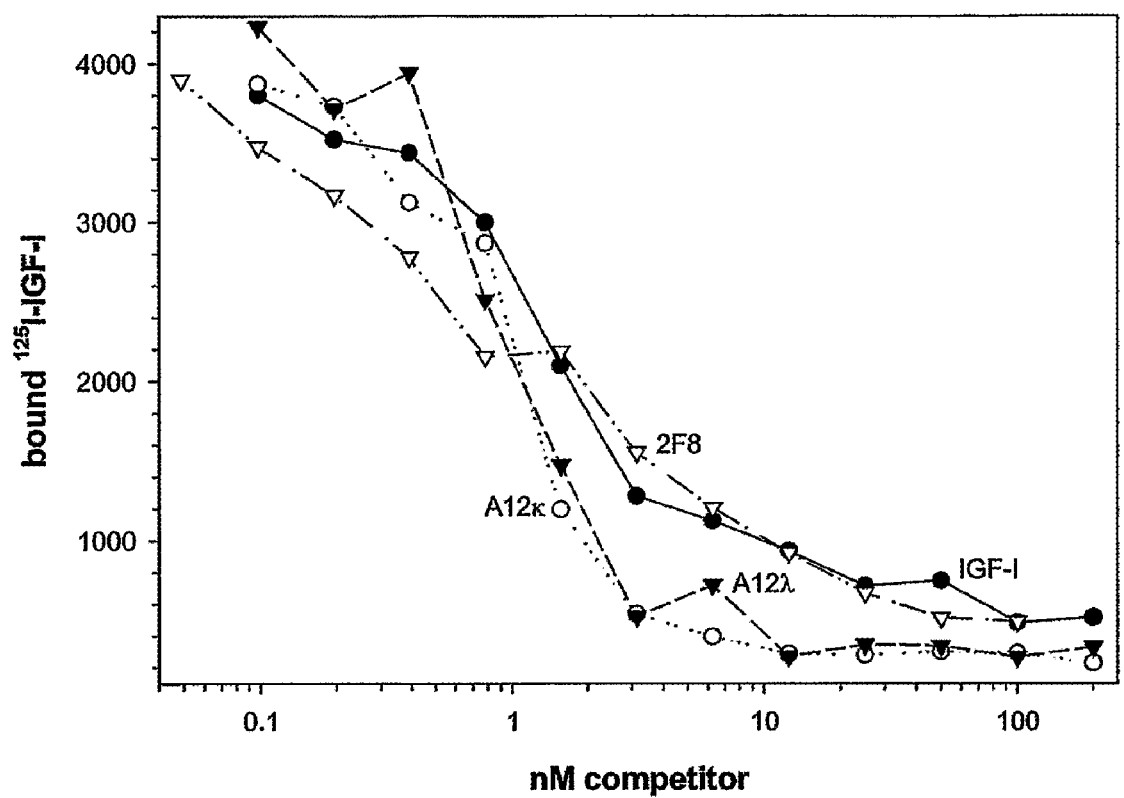
FIG. 15 shows results of an assay that measures the capacity of antibodies 2F8 and A12 to block binding of IGF-I to immobilized soluble IGF-IR. A12 antibodies having kappa or lambda light chain constant regions were tested.

The present invention provides antibodies and fragments thereof, specific for insulin-like growth factor-I receptor (IGF-IR), as well as isolated or purified polynucleotide sequences encoding the antibodies. In certain embodiments of the invention, human antibodies are provided. The antibodies can also be used in combination with other chemical and biological agents, including, but not limited to, anti-neoplastic agents and/or agents that are inhibitors of other receptors or receptor substrates mediating cell growth. The invention further relates to anti-neoplastic agents that are inhibitors of topoisomerase function. The choice of such agents is advantageous for use in therapeutic methods in combination with antibodies that are specific for IGF-IR.

Naturally occurring antibodies typically have two identical heavy chains and two identical light chains, with each light chain covalently linked to a heavy chain by an interchain disulfide bond and multiple disulfide bonds further link the two heavy chains to one another. Individual chains can fold into domains having similar sizes (110-125 amino acids) and structures, but different functions. The light chain can comprise one variable domain ($V_L$) and/or one constant domain ($C_L$). The heavy chain can also comprise one variable domain ($V_H$) and/or, depending on the class or isotype of antibody, three or four constant domains ($C_H1$, $C_H2$, $C_H3$ and $C_H4$). In humans, the isotypes are IgA, IgD, IgE, IgG, and IgM, with IgA and IgG further subdivided into subclasses or subtypes ($IgA_{1-2}$ and $IgG_{1-4}$).

Generally, the variable domains show considerable amino acid sequence variability from one antibody to the next, particularly at the location of the antigen-binding site. Three regions, called hypervariable or complementarity-determining regions (CDRs), are found in each of $V_L$ and $V_H$, which are supported by less variable regions called frameworks.

The portion of an antibody consisting of $V_L$ and $V_H$ domains is designated Fv (Fragment variable) and constitutes the antigen-binding site. Single chain Fv (scFv) is an antibody fragment containing a $V_L$ domain and a $V_H$ domain on one polypeptide chain, wherein the N terminus of one domain and the C terminus of the other domain are joined by a flexible linker (see, e.g., U.S. Pat. No. 4,946,778 (Ladner et al.); WO 88/09344, (Huston et al.). WO 92/01047 (McCafferty et al.) describes the display of scFv fragments on the surface of soluble recombinant genetic display packages, such as bacteriophage.

The peptide linkers used to produce the single chain antibodies can be flexible peptides selected to assure that the proper three-dimensional folding and association of the $V_L$ and $V_H$ domains occurs. The linker is generally 10 to 50 amino acid residues. Preferably, the linker is 10 to 30 amino acid residues. More preferably the linker is 12 to 30 amino acid residues. Most preferably is a linker of 15 to 25 amino acid residues. An non-limiting example of such a linker peptides is (Gly-Gly-Gly-Gly-Ser)$_3$ (SEQ ID NO:33).

Fab (Fragment, antigen binding) refers to the fragments of the antibody consisting of $V_L$-$C_L$ and $V_H$-$C_H1$ domains. Such a fragment generated by digestion of a whole antibody with papain does not retain the antibody hinge region by which two heavy chains are normally linked. The fragment is monovalent and simply referred to as Fab. Alternatively, digestion with pepsin results in a fragment that retains the hinge region. Such a fragment with intact interchain disulfide bonds linking two heavy chains is divalent and is referred to as $F(ab')_2$. A monovalent Fab' results when the disulfide bonds of an $F(ab')_2$ are reduced (and the heavy chains are separated. Because they are divalent, intact antibodies and $F(ab')_2$ fragments have higher avidity for antigen that the monovalent Fab or Fab' fragments. WO 92/01047 (McCafferty et al.) describes the display of Fab fragments on the surface of soluble recombinant genetic display packages, such as bacteriophage.

Fc (Fragment crystallization) is the designation for the portion or fragment of an antibody that consists of paired heavy chain constant domains. In an IgG antibody, for example, the Fc consists of heavy chain $C_H2$ and $C_H3$ domains. The Fc of an IgA or an IgM antibody further comprises a $C_H4$ domain. The Fc is associated with Fc receptor binding, activation of complement-mediated cytotoxicity and antibody-dependent cellular-cytotoxicity (ADCC). For antibodies such as IgA and IgM, which are complexes of multiple IgG like proteins, complex formation requires Fc constant domains.

Finally, the hinge region separates the Fab and Fc portions of the antibody, providing for mobility of Fabs relative to each other and relative to Fc, as well as including multiple disulfide bonds for covalent linkage of the two heavy chains.

Antibody formats have been developed which retain binding specificity, but have other characteristics that may be desirable, including for example, bispecificity, multivalence (more than two binding sites), compact size (e.g., binding domains alone).

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one $V_H$ and one $V_L$ domain covalently linked by a first peptide linker, can be covalently linked by at least one or more peptide linker to form a multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of amino acid residues is about one hundred.

Two single chain antibodies can be combined to form a diabody, also known as a bivalent dimer. Diabodies have two chains and two binding sites, and can be monospecific or bispecific. Each chain of the diabody includes a $V_H$ domain connected to a $V_L$ domain. The domains are connected with linkers that are short enough to prevent pairing between domains on the same chain, thus driving the pairing between complementary domains on different chains to recreate the two antigen-binding sites.

Three single chain antibodies can be combined to form triabodies, also known as trivalent trimers. Triabodies are constructed with the amino acid terminus of a $V_L$ or $V_H$ domain directly fused to the carboxyl terminus of a $V_L$ or $V_H$ domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Thus, antibodies of the invention and fragments thereof include, but are not limited to, naturally occurring antibodies, bivalent fragments such as $(Fab')_2$, monovalent fragments such as Fab, single chain antibodies, single chain Fv (scFv), single domain antibodies, multivalent single chain antibodies, diabodies, triabodies, and the like that bind specifically with antigens.

The antibodies of the present invention and particularly the variable domains thereof may be obtained by methods known in the art. These methods include, for example, the immunological method described by Kohler and Milstein, Nature, 256: 495-497 (1975) and Campbell, Monoclonal Antibody Technology, The Production and Characterization of Rodent and Human Hybridomas, Burdon et al., Eds., Laboratory Techniques in Biochemistry and Molecular Biology, Volume 13, Elsevier Science Publishers, Amsterdam (1985); as well as by the recombinant DNA methods such as described by Huse et al., Science, 246, 1275-81 (1989). The antibodies can also be obtained from phage display libraries bearing combinations of $V_H$ and $V_L$ domains in the form of scFv or Fab. The $V_H$ and $V_L$ domains can be encoded by nucleotides that are synthetic, partially synthetic, or naturally derived. In certain embodiments, phage display libraries bearing human antibody fragments can be preferred. Other sources of human antibodies are transgenic mice engineered to express human immunoglobulin genes.

Antibody fragments can be produced by cleaving a whole antibody, or by expressing DNA that encodes the fragment. Fragments of antibodies may be prepared by methods described by Lamoyi et al., *J. Immunol. Methods*, 56: 235-243 (1983) and by Parham, *J. Immunol.* 131: 2895-2902 (1983). Such fragments may contain one or both Fab fragments or the $F(ab')_2$ fragment. Such fragments may also contain single-chain fragment variable region antibodies, i.e. scFv, dibodies, or other antibody fragments. Methods of producing such functional equivalents are disclosed in PCT Application WO 93/21319, European Patent Application No. 239,400; PCT Application WO 89/09622; European Patent Application 338,745; and European Patent Application EP 332,424.

The antibodies, or fragments thereof, of the present invention are specific for IGF-IR. Antibody specificity refers to selective recognition of the antibody for a particular epitope of an antigen. Antibodies, or fragments thereof, of the present invention, for example, can be monospecific or bispecific. Bispecific antibodies (BsAbs) are antibodies that have two different antigen-binding specificities or sites. Where an antibody has more than one specificity, the recognized epitopes can be associated with a single antigen or with more than one antigen. Thus, the present invention provides bispecific antibodies, or fragments thereof, that bind to two different antigens, with at least one specificity for IGF-IR.

Specificity of the present antibodies, or fragments thereof, for IGF-IR can be determined based on affinity and/or avidity. Affinity, represented by the equilibrium constant for the dissociation of an antigen with an antibody (Kd), measures the binding strength between an antigenic determinant and an antibody-binding site. Avidity is the measure of the strength of binding between an antibody with its antigen. Avidity is related to both the affinity between an epitope with its antigen binding site on the antibody, and the valence of the antibody, which refers to the number of antigen binding sites specific for a particular epitope. Antibodies typically bind with a dissociation constant (Kd) of $10^{-5}$ to $10^{-11}$ liters/mol. Any Kd greater than $10^{-4}$ liters/mol is generally considered to indicate nonspecific binding. The lesser the value of the Kd, the stronger the binding strength between an antigenic determinant and the antibody binding site.

Antibodies of the present invention, or fragments thereof, also include those for which binding characteristics have been improved by direct mutation, methods of affinity maturation, phage display, or chain shuffling. Affinity and specificity can be modified or improved by mutating CDR and/or FW residues and screening for antigen binding sites having the desired characteristics (see, e.g., Yang et al., J. Mol. Biol., (1995) 254: 392-403). One way is to randomize individual residues or combinations of residues so that in a population of, otherwise identical antigen binding sites, subsets of from two to twenty amino acids are found at particular positions. Alternatively, mutations can be induced over a range of residues by error prone PCR methods (see, e.g., Hawkins et al., J. Mol. Biol., (1992) 226: 889-96). In another example, phage display vectors containing heavy and light chain variable region genes can be propagated in mutator strains of *E. coli* (see, e.g., Low et al., J. Mol. Biol., (1996) 250: 359-68). These methods of mutagenesis are illustrative of the many methods known to one of skill in the art.

Equivalents of the antibodies, or fragments thereof, of the present invention include polypeptides with amino acid sequences substantially the same as the amino acid sequence of the variable or hypervariable regions of the full-length anti-IGF-IR antibodies. Substantially the same amino acid sequence is defined herein as a sequence with at least 70%, preferably at least about 80%, and more preferably at least about 90% homology to another amino acid sequence, as determined by the FASTA search method in accordance with Pearson and Lipman (Proc. Natl. Acad. Sci. USA (1988) 85: 2444-8).

Conservative amino acid substitution is defined as a change in the amino acid composition by way of changing one or two amino acids of a peptide, polypeptide or protein, or fragment thereof. The substitution is of amino acids with generally similar properties (e.g., acidic, basic, aromatic, size, positively or negatively charged, polarity, non-polarity) such that the substitutions do not substantially alter peptide, polypeptide or protein characteristics (e.g., charge, isoelectric point, affinity, avidity, conformation, solubility) or activity. Typical substitutions that may be performed for such conservative amino acid substitution may be among the groups of amino acids as follows:

glycine (G), alanine (A), valine (V), leucine (L) and isoleucine (I);
aspartic acid (D) and glutamic acid (E);
alanine (A), serine (S) and threonine (T);
histidine (H), lysine (K) and arginine (R):
asparagine (N) and glutamine (Q);
phenylalanine (F), tyrosine (Y) and tryptophan (W)

Conservative amino acid substitutions can be made in, e.g., regions flanking the hypervariable regions primarily responsible for the selective and/or specific binding characteristics of the molecule, as well as other parts of the molecule, e.g., variable heavy chain cassette.

Each domain of the antibodies of this invention can be a complete antibody with the heavy or light chain variable domain, or it can be a functional equivalent or a mutant or derivative of a naturally-occurring domain, or a synthetic domain constructed, for example, in vitro using a technique such as one described in WO 93/11236 (Griffiths et al.). For instance, it is possible to join together domains corresponding to antibody variable domains, which are missing at least one amino acid. The important characterizing feature is the ability of each domain to associate with a complementary domain to form an antigen-binding site. Accordingly, the terms variable heavy and light chain fragment should not be construed to exclude variants that do not have a material effect on specificity.

In a preferred embodiment, the anti-IGF-IR antibodies of the present invention are human antibodies that exhibit one or more of following properties.

1) The antibodies bind to the external domain of IGF-IR and inhibit binding of IGF-I or IGF-II to IGF-IR. Inhibition can be determined, for example, by a direct binding assay using purified or membrane bound receptor. In this embodiment, the antibodies of the present invention, or fragments thereof, preferably bind IGF-IR at least as strongly as the natural ligands of IGF-IR (IGF-I and IGF-II).

2) The antibodies neutralize IGF-IR. Binding of a ligand, e.g., IGF-I or IGF-II, to an external, extracellular domain of IGF-IR stimulates autophosphorylation of the beta subunit and phosphorylation of IFG-IR substrates, including MAPK, Akt, and IRS-1.

Neutralization of IGF-IR includes inhibition, diminution, inactivation and/or disruption of one or more of these activities normally associated with signal transduction. Further, this includes inhibition of IGF-IR/IR heterodimers as well as IGF-IR homodimers. Thus, neutralizing IGF-IR has various effects, including inhibition, diminution, inactivation and/or disruption of growth (proliferation and differentiation), angiogenesis (blood vessel recruitment, invasion, and metastasis), and cell motility and metastasis (cell adhesion and invasiveness).

One measure of IGF-IR neutralization is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining neutralizing antibodies in the context of the present invention. Phosphorylation can be detected, for example, using an antibody specific for phosphotyrosine in an ELISA assay or on a western blot. Some assays for tyrosine kinase activity are described in Panek et al., *J. Pharmacol. Exp. Thera.* 283: 1433-44 (1997) and Batley et al., *Life Sci.* 62:143-50 (1998). Antibodies of the invention cause a decrease in tyrosine phosphorylation of IGF-IR of at least about 75%, preferably at least about 85%, and more preferably at least about 90% in cells that respond to ligand.

Another measure of IGF-IR neutralization is inhibition of phosphorylation of downstream substrates of IGF-IR. Accordingly, the level of phosphorylation of MAPK, Akt, or IRS-1 can be measured. The decrease in substrate phosphorylation is at least about 50%, preferably at least about 65%, more preferably at least about 80%.

In addition, methods for detection of protein expression can be utilized to determine IGF-IR neutralization, wherein the proteins being measured are regulated by IGF-IR tyrosine kinase activity. These methods include immunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA. See, e.g., Grandis et al., *Cancer,* 78:1284-92 (1996); Shimizu et al., *Japan J. Cancer Res.,* 85:567-71 (1994); Sauter et al., *Am. J. Path.,* 148:1047-53 (1996); Collins, *Glia* 15:289-96 (1995); Radinsky et al., *Clin. Cancer Res.* 1:19-31 (1995); Petrides et al., *Cancer Res.* 50:3934-39 (1990); Hoffmann et al., *Anticancer Res.* 17:4419-26 (1997); Wikstrand et al., *Cancer Res.* 55:3140-48 (1995).

In vivo assays can also be utilized to determine IGF-IR neutralization. For example, receptor tyrosine kinase inhibition can be observed by mitogenic assays using cell lines stimulated with receptor ligand in the presence and absence of inhibitor. For example, MCF7 (American Type Culture Collection (ATCC), Rockville, Md.) stimulated with IGF-I or IGF-II can be used to assay IGF-IR inhibition. Another method involves testing for inhibition of growth of IGF-IR-expressing tumor cells or cells transfected to express IGF-IR. Inhibition can also be observed using tumor models, for example, human tumor cells injected into a mouse.

The present invention is not limited by any particular mechanism of IGF-IR neutralization. The anti-IGF-IR antibodies of the present invention can bind externally to the IGF-IR cell surface receptor, block binding of ligand (e.g., IGF-I or IGF-II) and subsequent signal transduction mediated via the receptor-associated tyrosine kinase, and prevent phosphorylation of the IGF-IR and other downstream proteins in the signal transduction cascade.

3) The antibodies down modulate IGF-IR. The amount of IGF-IR present on the surface of a cell depends on receptor protein production, internalization, and degradation. The amount of IGF-IR present on the surface of a cell can be measured indirectly, by detecting internalization of the receptor or a molecule bound to the receptor. For example, receptor internalization can be measured by contacting cells that express IGF-IR with a labeled antibody. Membrane-bound antibody is then stripped, collected and counted. Internalized antibody is determined by lysing the cells and detecting label in the lysates.

Another way is to directly measure the amount of the receptor present on the cell following treatment with an anti-IGF-IR antibody or other substance, for example, by fluorescence-activated cell-sorting analysis of cells stained for surface expression of IGF-IR. Stained cells are incubated at 37° C. and fluorescence intensity measured over time. As a control, part of the stained population can be incubated at 4° C. (conditions under which receptor internalization is halted).

As described in the Examples, cell surface IGF-IR can be detected and measured using a different antibody that is specific for IGF-IR and that does not block or compete with binding of the antibody being tested. (Burtrum, et al. *Cancer Res.* 63:8912-21 (2003)) Treatment of an IGF-IR expressing cell with an antibody of the invention results in reduction of cell surface IGF-IR. In a preferred embodiment, the reduction is at least about 70%, more preferably at least about 80%, and even more preferably at least about 90% in response to treatment with an antibody of the invention. A significant decrease can be observed in as little as four hours.

Another measure of down-modulation is reduction of the total receptor protein present in a cell, and reflects degradation of internal receptors. Accordingly, treatment of cells (particularly cancer cells) with antibodies of the invention results in a reduction in total cellular IGF-IR. In a preferred embodiment, the reduction is at least about 70%, more preferably at least about 80%, and even more preferably at least about 90%.

The antibodies of the invention bind to IGF-IR with a $K_d$ of about $3\times10^{-10}$ M$^{-1}$ or less, preferably about $1\times10^{-10}$ M$^{-1}$ or less, and more preferably about $3\times10^{-11}$ M$^{-1}$ or less.

In an embodiment of the invention, the antibodies inhibit tumor growth. For example, subcutaneous xenograft tumors can be established by injection of cells of a cancer cell line into an immunodeficient mouse. The mice are then treated by intraperitoneal injection of antibodies, for example, every three days, and tumor size measured at regular intervals. Compared to control injections, antibodies of the invention inhibit tumor growth. In a preferred embodiment, an antibody of the invention promotes tumor regression when combined with an anti-neoplastic agent. Further, as exemplified below, in a more preferred embodiment, antibodies of the invention promoting tumor regression when used in a monotherapy. By promoting tumor regression is meant that administration of an effective amount of antibody, or an effective amount of a combination of an antibody and a neoplastic agent results in a reduction is size or necrosis of the tumor. In a preferred embodiment of the invention, tumor regression may be observed and continue for a period of at least about 20 days, more preferably at least about 40 days, more preferably at least about 60 days. Tumor regression may can be measured as an average across a group of subjects undergoing a particular treatment regimen, or can be measured by the number of subjects in a treatment group in which tumors regress.

Preferred antibodies of the present invention, or fragments thereof, are human antibodies having one, two, three, four, five, and/or six complementarity determining regions (CDRs) selected from the group consisting of SEQ ID NO:14, SEQ ID NO:16, SEQ ID NO:18, SEQ ID NO:20, SEQ ID NO:22, SEQ ID NO:24, SEQ ID NO:26, SEQ ID NO:28, and SEQ ID NO:30. Preferably, the antibodies (or fragments thereof) of the present invention have CDRs of SEQ ID NO:14, SEQ ID NO:16 and SEQ ID NO:18. Alternatively and also preferably, the present antibodies, or fragments thereof, have CDRs of SEQ ID NO:20, SEQ ID NO:22 and SEQ ID NO:24. Alternatively and also preferably, the present antibodies, or fragments thereof, have CDRs of SEQ ID NO:26, SEQ ID NO:28 and SEQ ID NO:30. The amino acid sequences of the CDRs are set forth below in Table 1.

TABLE 1

| Heavy Chain (2F8/A12) | | |
|---|---|---|
| CDR1 | SYAIS | SEQ ID NO: 14 |
| CDR2 | GIIPIFGTANYAQKFQG | SEQ ID NO: 16 |
| CDR3 | APLRFLEWSTQDHYYYYYMDV | SEQ ID NO: 18 |
| Light Chain (2F8) | | |
| CDR1 | QGDSLRSYYAS | SEQ ID NO: 20 |
| CDR2 | GKNNRPS | SEQ ID NO: 22 |
| CDR3 | NSRDNSDNRLI | SEQ ID NO: 24 |
| Light Chain (A12) | | |
| CDR1 | QGDSLRSYYAT | SEQ ID NO: 26 |
| CDR2 | GENKRPS | SEQ ID NO: 28 |
| CDR3 | KSRDGSGQHLV | SEQ ID NO: 30 |

In another embodiment, the present antibodies, or fragments thereof, can have a heavy chain variable region of SEQ ID NO: 2 and/or a light chain variable region selected from SEQ ID NO:6 or SEQ ID NO:10. IMC-A12 is a particularly preferred antibody of the present invention. This antibody has human $V_H$ and $V_L$ framework regions (FWs) as well as CDRs. The $V_H$ variable domain of IMC-A12 (SEQ ID NO:2) has three CDRs corresponding to SEQ ID NOs:14, 16, and 18 and the $V_L$ domain (SEQ ID NO:10) has three CDRs corresponding to SEQ ID NOS:26, 28, and 30. IMC-2F8 is another preferred antibody of the present invention. This antibody also has human $V_H$ and $V_L$ framework regions (FWs) and CDRs. The $V_H$ variable domain of IMC-2F8 is identical to the $V_H$ variable domain of IMCA12. The $V_L$ domain of IMC-2F8 (SEQ ID NO:6) has three CDRs corresponding to SEQ ID NOS:20, 22, and 24.

In another embodiment, antibodies of the invention compete for binding to IGF-IR with IMC-A12 and/or IMC-2F8. That is, the antibodies bind to the same or similar overlapping epitope.

The present invention also provides isolated polynucleotides encoding the antibodies, or fragments thereof, described previously. The invention includes nucleic acids having a sequence encoding one, two, three, four, five and/or all six CDRs as set forth in Table 2.

TABLE 2

Heavy Chain (2F8/A12)

| | | | |
|---|---|---|---|
| CDR1 | agctatgcta tcagc | | SEQ ID NO: 13 |
| CDR2 | gggatcatcc ctatctttgg tacagcaaac tacgcacaga agttccaggg c | | SEQ ID NO: 15 |
| CDR3 | gcgccattac gattttgga gtggtccacc caagaccact actactacta ctacatg gacgtc | | SEQ ID NO: 17 |

Light Chain (2F8)

| | | | |
|---|---|---|---|
| CDR1 | caaggagaca gcctcagaag ctattatgca agc | | SEQ ID NO: 19 |
| CDR2 | ggtaaaaaca accggccctc a | | SEQ ID NO: 21 |
| CDR3 | aactcccggg acaacagtga taaccgtctg ata | | SEQ ID NO: 23 |

Light Chain (A12)

| | | | |
|---|---|---|---|
| CDR1 | caaggagaca gcctcagaag ctattatgca acc | | SEQ ID NO: 25 |
| CDR2 | ggtgaaaata agcggccctc a | | SEQ ID NO: 27 |
| CDR3 | aaatctcggg atgcagtgg tcaacatctg gtg | | SEQ ID NO: 29 |

DNA encoding human antibodies can be prepared by recombining DNA encoding human constant regions and variable regions, other than the CDRs, derived substantially or exclusively from the corresponding human antibody regions and DNA encoding CDRs derived from a human (e.g., SEQ ID NOs:13, 15, and 17 for the heavy chain variable domain CDRs and SEQ ID NOs:19, 21, and 23 or SEQ ID NOS:25, 27 and 29 for the light chain variable domain CDRs).

Other suitable sources of DNAs that encode fragments of antibodies include any cell, such as hybridomas and spleen cells, that express the full-length antibody. The fragments may be used by themselves as antibody equivalents, or may be recombined into equivalents, as described above. The DNA recombinations and other techniques described in this section may be carried out by known methods. Other sources of DNAs are single chain antibodies or Fabs produced from a phage display library, as is known in the art.

Additionally, the present invention provides expression vectors containing the polynucleotide sequences previously described operably linked to an expression sequence, a promoter and an enhancer sequence. A variety of expression vectors for the efficient synthesis of antibody polypeptide in prokaryotic, such as bacteria and eukaryotic systems, including but not limited to yeast and mammalian cell culture systems have been developed. The vectors of the present invention can comprise segments of chromosomal, non-chromosomal and synthetic DNA sequences.

Any suitable expression vector can be used. For example, prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages. An example of a vector useful in yeast is the 2μ plasmid. Suitable vectors for expression in mammalian cells include well-known derivatives of SV-40, adenovirus, retrovirus-derived DNA sequences and shuttle vectors derived from combination of functional mammalian vectors, such as those described above, and functional plasmids and phage DNA.

Additional eukaryotic expression vectors are known in the art (e.g., P. J. Southern and P. Berg, *J. Mol. Appl. Genet.* 1: 327-41 (1982); Subramani et al., *Mol. Cell. Biol.* 1: 854-64 (1981); Kaufmann and Sharp, "Amplification And Expression of Sequences Cotransfected with a Modular Dihydrofolate Reductase Complementary DNA Gene," *J. Mol. Biol.* 159: 601-21 (1982); Kaufmann and Sharp, *Mol. Cell. Biol.* 159: 601-64 (1982); Scahill et al., "Expression And Characterization Of The Product Of A Human Immune Interferon DNA Gene In Chinese Hamster Ovary Cells," *Proc. Nat'l Acad. Sci. USA* 80, 4654-59 (1983); Urlaub and Chasin, *Proc. Nat'l Acad. Sci. USA* 77: 4216-20, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Where it is desired to express a gene construct in yeast, a suitable selection gene for use in yeast is the trp1 gene present in the yeast plasmid YRp7. Stinchcomb et al. *Nature*, 282: 39 (1979); Kingsman et al., *Gene*, 7: 141 (1979). The trp1 gene provides a selection marker for a mutant strain of yeast lacking the ability to grow in tryptophan, for example, ATCC No. 44076 or PEP4-1. Jones, *Genetics*, 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

The present invention also provides recombinant host cells containing the expression vectors previously described. Antibodies of the present invention can be expressed in cell lines other than in hybridomas. Nucleic acids, which comprise a sequence encoding a polypeptide according to the invention, can be used for transformation of a suitable mammalian host cell.

Cell lines of particular preference are selected based on high level of expression, constitutive expression of protein of interest and minimal contamination from host proteins. Mammalian cell lines available as hosts for expression are well known in the art and include many immortalized cell lines, such as but not limited to, COS-7 cells, Chinese Hamster Ovary (CHO) cells, Baby Hamster Kidney (BHK) cells and many others including cell lines of lymphoid origin such as lymphoma, myeloma, or hybridoma cells. Suitable additional eukaryotic cells include yeast and other fungi. Useful prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas, Bacillus*, such as *Bacillus subtilis*, and *Streptomyces*.

These present recombinant host cells can be used to produce an antibody, or fragment thereof, by culturing the cells under conditions permitting expression of the antibody or fragment thereof and purifying the antibody or fragment thereof from the host cell or medium surrounding the host cell. Targeting of the expressed antibody or fragment for secretion in the recombinant host cells can be facilitated by inserting a signal or secretory leader peptide-encoding sequence (see, Shokri et al., *Appl Microbiol Biotechnol.* 60:654-64 (2003) Nielsen et al., *Prot. Eng.* 10:1-6 (1997) and von Heinje et al., *Nucl. Acids Res.* 14:4683-90 (1986)) at the 5' end of the antibody-encoding gene of interest. These secretory leader peptide elements can be derived from either prokaryotic or eukaryotic sequences. Accordingly suitably, secretory leader peptides are used, being amino acids joined to the N-terminal end of a polypeptide to direct movement of the polypeptide out of the host cell cytosol and secretion into the medium.

The transformed host cells are cultured by methods known in the art in a liquid medium containing assimilable sources of carbon (carbohydrates such as glucose or lactose), nitrogen (amino acids, peptides, proteins or their degradation products such as peptones, ammonium salts or the like), and inorganic salts (sulfates, phosphates and/or carbonates of sodium, potassium, magnesium and calcium). The medium furthermore contains, for example, growth-promoting substances, such as trace elements, for example iron, zinc, manganese and the like.

Another embodiment for the preparation of antibodies in the present invention is the expression of the nucleic acid encoding the antibody according to the invention in a transgenic animal that has a substantial portion of the human antibody producing genome inserted and is rendered deficient in the production of endogenous antibodies. Transgenic animals, include but not limited to mice, goat, and rabbit. One further embodiment of the invention, include expression of the antibody-coding gene in, for example, the mammary gland of the animal for secretion of the polypeptide during lactation.

As described in the examples below, high affinity anti-IGF-IR antibodies according to the present invention can be isolated from a phage display library constructed from human heavy chain and light chain variable region genes. For example, a variable domain of the invention can be obtained from a peripheral blood lymphocyte that contains a rearranged variable region gene. Alternatively, variable domain portions, such as CDR and FW regions, can be derived from different human sequences. Over 90% of recovered clones after three rounds of selection are specific to IGF-IR. The binding affinities for IGF-IR of the screened Fabs can be in the nM range, which is as high as many bivalent anti-IGF-IR monoclonal antibodies produced using hybridoma technology.

Antibodies, and fragments thereof, of the present invention can be obtained, for example, from naturally occurring antibodies, or Fab or scFv phage display libraries. Single domain antibodies can be obtained by selecting a $V_H$ or a $V_L$ domain from a naturally occurring antibody or hybridoma, or selected from a library of $V_H$ domains or a library of $V_L$ domains. It is understood that amino acid residues that are primary determinants of binding of single domain antibodies can be within Kabat defined CDRs, but may include other residues as well, such as, for example, residues that would otherwise be buried in the $V_H$-$V_L$ interface of a $V_H$-$V_L$ heterodimer.

Antibodies of the present invention also include those for which binding characteristics have been improved by direct mutation, methods of affinity maturation, phage display, or chain shuffling. Affinity and specificity may be modified or improved by mutating CDRs and screening for antigen binding sites having the desired characteristics (see, e.g., Yang et al., *J. Mol. Biol.*, 254: 392-403 (1995)). CDRs are mutated in a variety of ways. One way is to randomize individual residues or combinations of residues so that in a population of otherwise identical antigen binding sites, all twenty amino acids are found at particular positions. Alternatively, mutations are induced over a range of CDR residues by error prone PCR methods (see, e.g., Hawkins et al., *J. Mol. Biol.*, 226: 889-896 (1992)). For example, phage display vectors containing heavy and light chain variable region genes may be propagated in mutator strains of *E. coli* (see, e.g., Low et al., *J. Mol. Biol.*, 250: 359-368 (1996)). These methods of mutagenesis are illustrative of the many methods known to one of skill in the art.

The protein used to identify IGF-IR binding antibodies of the invention is preferably IGF-RI and, more preferably, is the extracellular domain of IGF-RI. The IGF-RI extracellular domain can be free or conjugated to another molecule.

The antibodies of this invention can be fused to additional amino acid residues. Such amino acid residues can be a peptide tag, perhaps to facilitate isolation. Other amino acid residues for homing of the antibodies to specific organs or tissues are also contemplated.

In another aspect of the invention, anti-IGF-IR antibodies or antibody fragments can be chemically or biosynthetically linked to anti-tumor agents or detectable signal-producing agents. As exemplified below, antibodies of the invention are efficiently internalized upon binding to cells bearing IGF-IR. Anti-tumor agents linked to an antibody include any agents which destroy or damage a tumor to which the antibody has bound or in the environment of the cell to which the antibody has bound. For example, an anti-tumor agent is a toxic agent such as a chemotherapeutic agent or a radioisotope. Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents are conjugated to the antibody using conventional methods (See, e.g., Hermentin and Seiler, *Behring Inst. Mitt.* 82:197-215 (1988)).

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible region, and can be substrates or degradation products of enzyme catalyzed reactions.

The invention further contemplates anti-IGF-IR antibodies or antibody fragments of the invention to which target or reporter moieties are linked. Target moieties are first members of binding pairs. Anti-tumor agents, for example, are conjugated to second members of such pairs and are thereby directed to the site where the antigen-binding protein is bound. A common example of such a binding pair is avidin and biotin. In a preferred embodiment, biotin is conjugated to an antigen-binding protein of the invention, and thereby provides a target for an anti-tumor agent or other moiety which is conjugated to avidin or streptavidin. Alternatively, biotin or another such moiety is linked to an antigen-binding protein of the invention and used as a reporter, for example in a diagnostic system where a detectable signal-producing agent is conjugated to avidin or streptavidin.

Suitable radioisotopes for use as anti-tumor agents are also known to those skilled in the art. For example, $^{131}$I or $^{211}$At is used. These isotopes are attached to the antibody using conventional techniques (See, e.g., Pedley et al., *Br. J. Cancer* 68, 69-73 (1993)). Alternatively, the anti-tumor agent which is attached to the antibody is an enzyme which activates a prodrug. In this way, a prodrug is administered which remains in its inactive form until it reaches the tumor site where it is converted to its cytotoxin form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4) or tumor necrosis factor alpha (TNF-$\alpha$). The antibody targets the cytokine to the tumor so that the cytokine mediates damage to or destruction of the tumor without affecting other tissues. The cytokine is fused to the antibody at the DNA level using conventional recombinant DNA techniques.

A method of treating tumor growth in a mammal by administering to the mammal an effective amount of an antibody as previously described is also provided by the present invention. The IGF-IR signaling pathway has been extensively demonstrated to be a causative factor in the development of many types of cancer. IGF-I and IGF-II have been shown to be strong mitogens for a wide variety of cancer cell lines, including prostate, breast, colon, myeloma, ovary, pancreas and lung. Further, highly metastatic cancer cells have been shown to express higher levels of IGF-IR and IGF-II than tumor cells less prone to metastasize.

Suitable tumors to be treated according to the present invention preferably express IGF-IR. While not intended to be bound to any particular mechanism, the diseases and conditions which can be treated or prevented by the present methods include, for example, those in which pathogenic angiogenesis or tumor growth is stimulated through an IGF-IR paracrine and/or autocrine loop. For example, highly metastatic tumors tend to express both IGF-II and IGF-IR.

In an embodiment of the invention, anti-IGF-IR antibodies can be administered in combination with one or more other anti-neoplastic agents. For examples of combination therapies, see, e.g., U.S. Pat. No. 6,217,866 (Schlessinger et al.) (Anti-EGFR antibodies in combination with anti-neoplastic agents); WO 99/60023 (Waksal et al.) (Anti-EGFR antibodies in combination with radiation). Any suitable anti-neoplastic agent can be used, such as a chemotherapeutic agent, radiation or combinations thereof. The anti-neoplastic agent can be an alkylating agent or an anti-metabolite. Examples of alkylating agents include, but are not limited to, cisplatin, cyclophosphamide, melphalan, and dacarbazine. Examples of anti-metabolites include, but are not limited to, doxorubicin, daunorubicin, and paclitaxel, gemcitabine, and topoisomerase inhibitors irinotecan (CPT-11), aminocamptothecin, camptothecin, DX-8951f, and topotecan (topoisomerase I) and etoposide (VP-16) and teniposide (VM-26) (topoisomerase II). When the anti-neoplastic agent is radiation, the source of the radiation can be either external (external beam radiation therapy—EBRT) or internal (brachytherapy—BT) to the patient being treated. The dose of antineoplastic agent administered depends on numerous factors, including, for example, the type of agent, the type and severity tumor being treated and the route of administration of the agent. It should be emphasized, however, that the present invention is not limited to any particular dose.

The anti-neoplastic agents which are presently known in the art or being evaluated can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti survival agents, biological response modifiers, anti-hormones, and anti-angiogenesis agents.

Among these classes, the data reported herein suggest that topoisomerase inhibitors are particularly effective anti-neoplastic agents when used in combination with antibodies that bind to IGF-IR. Accordingly, embodiments of the invention include methods in which a topoisomerase inhibitor is administered in combination with an antibody that binds to IGF-IR. The inhibitors can be inhibitors of topoisomerase I or topoisomerase II. Topoisomerase I inhibitors include irinotecan (CPT-11), aminocamptothecin, camptothecin, DX-8951f, topotecan. Topoisomerase II inhibitors include etoposide (VP-16), and teniposide (VM-26). Other substances are currently being evaluated with respect to topoisomerase inhibitory activity and effectiveness as anti-neoplastic agents. In a preferred embodiment, the topoisomerase inhibitor is irinotecan (CPT-11). The antibodies used in combination are antibodies of the invention that bind to IGF-IR and have at least one of the following properties: (i) inhibit binding of IGF-I or IGF-II to IGF-IR; (ii) neutralize activation of IGF-IR by IGF-I or IGF-II; (iii) reduce IGF-IR surface receptor; and bind to IGF-IR with a Kd of about $1\times10^{-10}$ M$^{-1}$ or less. In a more preferred embodiment, the antibodies to be used in combination with a topoisomerase inhibitor have the characteristics of the human antibodies set forth above.

Anti-IGF-IR antibodies of the invention can be administered with antibodies that neutralize other receptors involved in tumor growth or angiogenesis. In an embodiment of the invention, an anti-IGF-IR antibody is used in combination with a receptor antagonist that binds specifically to EGFR. Particularly preferred are antigen-binding proteins that bind to the extracellular domain of EGFR and block binding of one or more of its ligands and/or neutralize ligand-induced activation of EGFR. An EGFR antagonist can be an antibody that binds to EGFR or a ligand of EGFR and inhibits binding of EGFR to its ligand. Ligands for EGFR include, for example, EGF, TGF-$\alpha$, amphiregulin, heparin-binding EGF (HB-EGF) and betacellulin. EGF and TGF-$\alpha$ are thought to be the main endogenous ligands that result in EGFR-mediated stimulation, although TGF-$\alpha$ has been shown to be more potent in promoting angiogenesis. It should be appreciated that the EGFR antagonist can bind externally to the extracellular portion of EGFR, which can or can not inhibit binding of the ligand, or internally to the tyrosine kinase domain. Examples of EGFR antagonists that bind EGFR include, without limitation, biological molecules, such as antibodies (and functional equivalents thereof) specific for EGFR, and small molecules, such as synthetic kinase inhibitors that act directly on the cytoplasmic domain of EGFR.

Another example of such a receptor is VEGFR. In an embodiment of the present invention, an anti-IGF-IR antibody is used in combination with a VEGFR antagonist. In one embodiment of the invention, an anti-IGF-IR antibody is used in combination with a receptor antagonist that binds specifically to VEGFR-1/Flt-1 receptor. In another embodiment, an anti-IGF-IR antibody is used in combination with a receptor antagonist that binds specifically to VEGFR-2/KDR receptor. Particularly preferred are antigen-binding proteins that bind to the extracellular domain of VEGFR-1 or VEGFR-2 and block binding by their ligands (VEGFR-2 is stimulated most strongly by VEGF; VEGFR-1 is stimulated most strongly by P1GF, but also by VEGF) and/or neutralize ligand-induced induced activation. For example, IMC-1121 is a human antibody that binds to and neutralizes VEGFR-2 (WO 03/075840; Zhu). Another example is MAb 6.12 is a scFv that binds to soluble and cell surface-expressed VEGFR-1. ScFv 6.12 comprises the $V_L$ and $V_H$ domains of mouse monoclonal antibody MAb 6.12. A hybridoma cell line producing MAb 6.12 has been deposited as ATCC number PTA-3344 under the provisions of the Budapest Treaty on the International Recognition of the Deposit of Microorganisms for the Purposes of Patent Procedure and the regulations thereunder (Budapest Treaty).

Other examples of growth factor receptors involved in tumorigenesis are the receptors for platelet-derived growth factor (PDGFR), nerve growth factor (NGFR), and fibroblast growth factor (FGFR).

In an additional alternative embodiment, the IGF-IR antibody can be administered in combination with one or more suitable adjuvants, such as, for example, cytokines (IL-10 and IL-13, for example) or other immune stimulators, such as, but not limited to, chemokine, tumor-associated antigens, and peptides. See, e.g., Larrivée et al., supra. It should be appreciated, however, that administration of only an anti-IGF-IR antibody is sufficient to prevent, inhibit, or reduce the progression of the tumor in a therapeutically effective manner.

In a combination therapy, the anti-IGF-IR antibody is administered before, during, or after commencing therapy with another agent, as well as any combination thereof, i.e., before and during, before and after, during and after, or before, during and after commencing the anti-neoplastic agent therapy. For example, the anti-IGF-IR antibody can be administered between 1 and 30 days, preferably 3 and 20 days, more preferably between 5 and 12 days before commencing radiation therapy. In a preferred embodiment of the invention, chemotherapy is administered concurrently with or, more preferably, subsequent to antibody therapy.

In the present invention, any suitable method or route can be used to administer anti-IGF-IR antibodies of the invention, and optionally, to co-administer anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific anti-tumor antibodies and specific anti-neoplastic agents, which will be determined on a patient to patient basis. Routes of administration include, for example, oral, intravenous, intraperitoneal, subcutaneous, or intramuscular administration. The dose of antagonist administered depends on numerous factors, including, for example, the type of antagonists, the type and severity tumor being treated and the route of administration of the antagonists. It should be emphasized, however, that the present invention is not limited to any particular method or route of administration.

It is noted that an anti-IGF-IR antibody of the invention can be administered as a conjugate, which binds specifically to the receptor and delivers a toxic, lethal payload following ligand-toxin internalization. The antibody-drug/small molecule conjugate can be directly linked to each other or via a linker, peptide or non-peptide.

In another aspect of the invention, an anti-IGF-IR antibody of the invention can be chemically or biosynthetically linked to one or more anti-neoplastic or anti-angiogenic agents.

The invention further contemplates anti-IGF-IR antibodies to which target or reporter moieties are linked. Target moieties are first members of binding pairs. Anti-neoplastic agents, for example, are conjugated to second members of such pairs and are thereby directed to the site where the anti-IGF-IR antibody is bound. A common example of such a binding pair is avidin and biotin. In a preferred embodiment, biotin is conjugated to an anti-IGF-IR antibody, and thereby provides a target for an anti-neoplastic agent or other moiety, which is conjugated to avidin or streptavidin. Alternatively, biotin or another such moiety is linked to an anti-IGF-IR antibody of the invention and used as a reporter, for example in a diagnostic system where a detectable signal-producing agent is conjugated to avidin or streptavidin.

It is understood that the anti-IGF-IR antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The present invention also includes kits for inhibiting tumor growth and/or angiogenesis comprising a therapeutically effective amount of a human anti-IGF-IR antibody. The kits can further contain any suitable antagonist of, for example, another growth factor receptor involved in tumorigenesis or angiogenesis (e.g., EGFR, VEGFR-1/Flt-1, VEGFR-2, PDGFR, NGFR, FGFR, etc, as described above). Alternatively, or in addition, the kits of the present invention can further comprise an anti-neoplastic agent. Examples of suitable anti-neoplastic agents in the context of the present invention have been described herein. The kits of the present invention can further comprise an adjuvant; examples have also been described above.

Moreover, included within the scope of the present invention is use of the present antibodies in vivo and in vitro for investigative or diagnostic methods, which are well known in the art. The diagnostic methods include kits, which contain antibodies of the present invention.

Accordingly, the present receptor antibodies thus can be used in vivo and in vitro for investigative, diagnostic, prophylactic, or treatment methods, which are well known in the art. Of course, it is to be understood and expected that variations in the principles of invention herein disclosed can be made by one skilled in the art and it is intended that such modifications are to be included within the scope of the present invention.

EXAMPLES

The following examples further illustrate the invention, but should not be construed to limit the scope of the invention in any way. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J et al., (1989) Molecular Cloning: A Laboratory Manual, $2^{nd}$ ed., Cold Spring Harbor Laboratory Press; and Coligan, J. et al. (1994) Current Protocols in Immunology, Wiley & Sons, Incorporated All references mentioned herein are incorporated in their entirety.

Selection and Engineering of Anti-Human IGF-IR Monoclonal Antibodies.

In order to isolate high affinity antibodies to the human IGF-I receptor, recombinant extracellular portion of human IGF-IR was used to screen a human naïve (non-immunized) bacteriophage Fab library containing $3.7 \times 10^{10}$ unique clones (de Haard et al., *J. Biol. Chem.* 274:18218-30 (1999)). Soluble IGF-IR (50 μg/ml) was coated onto tubes and blocked with 3% milk/PBS at 37 degrees for 1 hour. Phage were prepared by growing library stock to log phase culture, rescuing with M13K07 helper phage, and amplifying overnight at 30° C. in 2YTAK culture medium at containing ampicillin and kanamycin selection. The resulting phage preparation was precipitated in 4% PEG/0.5M NaCl and resuspended in 3% milk/PBS. The immobilized receptors were then incubated with phage preparation for 1 hour at room temperature. Afterwards, the tubes were washed 10 times with PBST (PBS containing 0.1% Tween-20) followed by 10 times with PBS. The bound phage were eluted at RT for 10 min with 1 ml of a freshly prepared solution of 100 mM triethylamine. The eluted phage were incubated with 10 ml of mid-log phase TG1 cells at 37° C. for 30 min stationary and 30 min shaking. The infected TG1 cells were pelleted and plated onto several large 2YTAG plates and incubated overnight at 30° C. All colonies that grew on the plates were scraped into 3 to 5 ml of 2YTA medium, mixed with glycerol (final concentration: 10%), aliquoted and stored at −70° C. For second round selection, 100 μl of the phage stock was added to 25 ml of 2YTAG medium and grown to mid-log phase. The culture was rescued with M13K07 helper phage, amplified, precipitated, and used for selection following the procedure described above, but with reduced concentration (5 μg/ml) of IGF-IR immobilized onto tubes and increasing the numbers of washes following the binding process. A total of two rounds of selection were performed.

Individual TG1 clones were picked and grown at 37° C. in 96 well plates and rescued with M13K07 helper phage as described above. The amplified phage preparation was blocked with 1/6 volume of 18% milk/PBS at RT for 1 h and added to Maxi-sorb 96-well microtiter plates (Nunc) coated with IGF-IR (1 μg/ml×1000. After incubation at RT for 1 h the plates were washed 3 times with PBST and incubated with a mouse anti-M13 phage-HRP conjugate (Amersham Pharmacia Biotech, Piscataway, N.J.). The plates were washed 5 times, TMB peroxidase substrate (KPL, Gaithersburg, Md.) added, and the absorbance at 450 nm read using a microplate reader (Molecular Device, Sunnyvale, Calif.). From 2 rounds of selection, 80% of independent clones were positive for binding to IGF-IR.

The diversity of the anti-IGF-IR Fab clones after the second round of selection was analyzed by restriction enzyme digestion pattern (i.e., DNA fingerprint). The Fab gene insert of individual clones was PCR amplified using primers: PUC19 reverse (5'-AGCGGATAACAATTTCACACAGG-3'; SEQ ID NO:31) and fdtet seq (5'-GTCGTCTTTCCA-GACGTTAGT-3'; SEQ ID NO:32) which are specific for sequences flanking the unique Fab gene regions within the phage vector. Each amplified product was digested with a frequent-cutting enzyme, BstN I, and analyzed on a 3% agarose gel. A total of 25 distinct patterns were identified. DNA sequences of representative clones from each digestion pattern were determined by dideoxynucleotide sequencing.

Plasmids from individual clones exhibiting positive binding to IGF-IR and unique DNA profile were used to transform a nonsuppressor *E. coli* host HB2151. Expression of the Fab fragments in HB2151 was induced by culturing the cells in 2YTA medium containing 1 mM isopropyl-1-thio-β-D-galactopyranoside (IPTG, Sigma) at 30° C. A periplasmic extract of the cells was prepared by resuspending the cell pellet in 25 mM Tris (pH 7.5) containing 20% (w/v) sucrose, 200 mM NaCl, 1 mM EDTA and 0.1 mM PMSF, followed by incubation at 4° C. with gentle shaking for 1 h. After centrifugation at 15,000 rpm for 15 min, the soluble Fab protein was purified from the supernatant by affinity chromatography using Protein G column followed the manufacturer's protocol (Amersham Pharmacia Biotech).

Candidate binding Fab clones were screened for competitive blocking of radiolabeled human IGF-I ligand to immobilized IGF-IR (100 ng/well) coated onto 96 strip-well plates. Fab preparations were diluted and incubated with IGF-IR plates for 0.5-1 hour at room temperature in PBS/0.1% BSA. Forty 40 pM of $^{125}$I-IGF-I was then added and the plates incubated an additional 90 minutes. Wells were then washed 3 times with ice-cold PBS/0.1% BSA, dried, and then counted in a gamma scintillation counter. Candidates that exhibited greater than 30% inhibition of control radiolabeled ligand binding in single point assay were selected and in vitro blocking titers determined Four clones were identified. Of these, only Fab clone 2F8 was shown to inhibit ligand binding by more than 50%, with an $IC_{50}$ of approximately 200 nM, and it was selected for conversion to full length IgG1 format. The heavy chain variable region sequence and translated amino acid sequence for 2F8 is shown in FIGS. 1 and 2, respectively. The DNA sequence and translated polypeptide sequence of the 2F8 heavy chain engineered as full length IgG1 are shown in FIGS. 3 and 4, respectively.

Fab 2F8 sequencing determined that this Fab possessed a lambda light chain constant region. The DNA sequence and translated amino acid sequence of the 2F8 light chain are shown in FIGS. 5 and 6, respectively. The sequences for full-length lambda light chain format are shown in FIGS. 7 and 8. Binding kinetic analysis was performed on 2F8 IgG using a BIAcore unit. This antibody was determined to bind to the IGF-IR with an affinity of 0.5-1 nM ($0.5-1 \times 10^{-9}$ M).

In order to improve the affinity of this antibody, a second generation Fab phage library was generated in which the 2F8 heavy chain was conserved and the light chain was varied to a diversity of greater than $10^8$ unique species. This method is termed light chain shuffling and has been used successfully to affinity mature selected antibodies for a given target antigen (Chames et al., *J. Immunol.* 169:1110-18 (2002)). This library was then screened for binding to the human IGF-IR (10 μg/ml) following procedures as described above, and the panning process repeated an additional three rounds with reduced IGF-IR concentration (2 μg/ml) for enrichment of high affinity binding Fabs. Seven clones were analyzed following round four. All 7 contained the same DNA sequence and restriction digest profile. The single isolated Fab was designated A12 and shown to possess a lambda light chain constant region. The light chain DNA sequence is shown in FIG. 9 and amino acid sequence in FIG. 10. Complete lambda light chain sequence and translated polypeptide sequence are shown in FIGS. 11 and 12, respectively. Amino acid sequence comparison of 2F8 and A12 light chains determined that the two variable regions differed by a total of 11 amino acids (refer to FIGS. 13 and 14). Nine of the changes were present within CDR regions, with the majority (6 amino acid residues) occurring within CDR3.

A comparison of the two antibody (full IgG) affinities for human IGF-IR and their ligand blocking activity is shown in Table 3. Binding results were determined by human IGF-IR ELISA and represent the concentration of titered antibody necessary to achieve 50% binding relative to saturation. Blocking results represent the level of antibody necessary to inhibit 50% binding of $^{125}$I-IGF-I ligand to immobilized human IGF-IR. Affinity was determined by BIAcore analysis according to manufacturer's specifications (Pharmacia BIA-CORE 3000). Soluble IGF-IR was immobilized on the sensor chips and antibody binding kinetics determined.

TABLE 3

Antibody binding characteristics

| Antibody | Binding (ED$_{50}$) | Blocking (EC$_{50}$) | Affinity |
|---|---|---|---|
| 2F8 | 2.0 nM | 3-6 nM | $K_D = 6.5 \times 10^{-10}$ |
|  |  |  | $K_{on} = 2.8 \times 10^5$ |
|  |  |  | $K_{off} = 1.8 \times 10^{-4}$ |
| A12 | 0.3 nM | 0.6-1 nM | $K_D = 4.1 \times 10^{-11}$ |
|  |  |  | $K_{on} = 7.2 \times 10^5$ |
|  |  |  | $K_{off} = 3.0 \times 10^{-5}$ |

The antibody changes incurred in 2F8 light chain to generate antibody A12 effected a significantly higher affinity of A12 for IGF-IR than 2F8. Concomitantly, this increase effected a greater binding ability of A12 for the receptor, as determined by ELISA, and at least a three-fold increase in blocking activity of ligand for immobilized receptor. FIG. 15 shows a representative titration of the two anti-IGF-IR antibodies in receptor blocking assay. The activity of A12 remained the same, irrespective of whether the light chain was engineered with a human lambda or kappa class constant region. Antibody A12 engineered with a lambda class light chain was utilized in all subsequent procedures. In this assay, A12 inhibited the binding of radiolabeled IGF-I to IGF-IR to a greater extent than competition with cold ligand. The activity of 2F8 was comparable to competition with cold ligand. This is consistent with the relative affinities of the two antibodies (see Table 3) and IGF-I (0.5-1 nM).

Engineering and Expression of Fully Human IgG1 Anti-IGF-IR Antibodies from Fab Clones.

The DNA sequences encoding the heavy and light chain genes of Fabs 2F8 and A12 were amplified by polymerase chain reaction (PCR) using the Boerhinger Mannheim Expand kit according to manufacturer's instructions. Forward and reverse primers contained sequences for restriction endonuclease sites for cloning into mammalian expression vectors. The recipient vector for the heavy chain contained the entire human gamma 1 constant region cDNA sequence, flanked by a strong eukaryotic promoter and a 3' polyadenylation sequence. The full-length lambda light chain sequences for 2F8 or A12 were each cloned in to a second vector possessing only the eukaryotic regulatory elements for expression in mammalian cells. A selectable marker was also present on this vector for selection of stable DNA integrants following transfection of the plasmid into mammalian cells. Forward primers were also engineered with sequences encoding a strong mammalian signal peptide sequence for proper secretion of the expressed antibody. Following identification of properly cloned immunoglobulin gene sequences, the DNAs were sequenced and tested for expression in transient transfection. Transient transfection was performed into the COST primate cell line using Lipofection, according to manufacturer's specifications. At 24 or 48 hours post-transfection, the expression of full IgG antibody was detected in conditioned culture supernatant by anti-human-Fc binding ELISA. ELISA Plates (96 well) were prepared by coating with 100 ng/well of a goat-anti-human Fc-specific polyclonal antibody (Sigma) and blocked with 5% milk/PBS overnight at 4° C. The plates were then washed 5 times with PBS. Conditioned supernatant was added to wells and incubated for 1.5 hours at room temperature. Bound antibody was detected with a goat anti-human lambda light chain-HRP antibody (Sigma) and visualized with TMB reagents and microplate reader as described above. Large scale preparation of anti-IGF-IR antibodies was achieved by either large scale transient transfection into COS cells, by scale-up of the Lipofection method or by stable transfection into a suitable host cell such as a mouse myeloma cell line (NS0, Sp2/0) or a Chinese hamster ovary cell line (CHO). Plasmid encoding the anti-IGF-IR antibodies were transfected into host cells by electroporation and selected in appropriate drug selection medium for approximately two weeks. Stably selected colonies were screened for antibody expression by anti-Fc ELISA and positive clones expanded into serum free cell culture medium. Antibody production from stably transfected cells was performed in suspension culture in spinner flasks or bioreactors for a period of up to two weeks. Antibody generated by either transient or stable transfection was purified by ProA affinity chromatography (Harlow and Lane. Antibodies. A Laboratory Manual. Cold Spring Harbor Press. 1988), eluted into a neutral buffered saline solution, and quantitated.

Determination of Ligand Blocking Activity of Anti-IGF-IR Monoclonal Antibodies on Human Tumor Cells.

Figure 16:
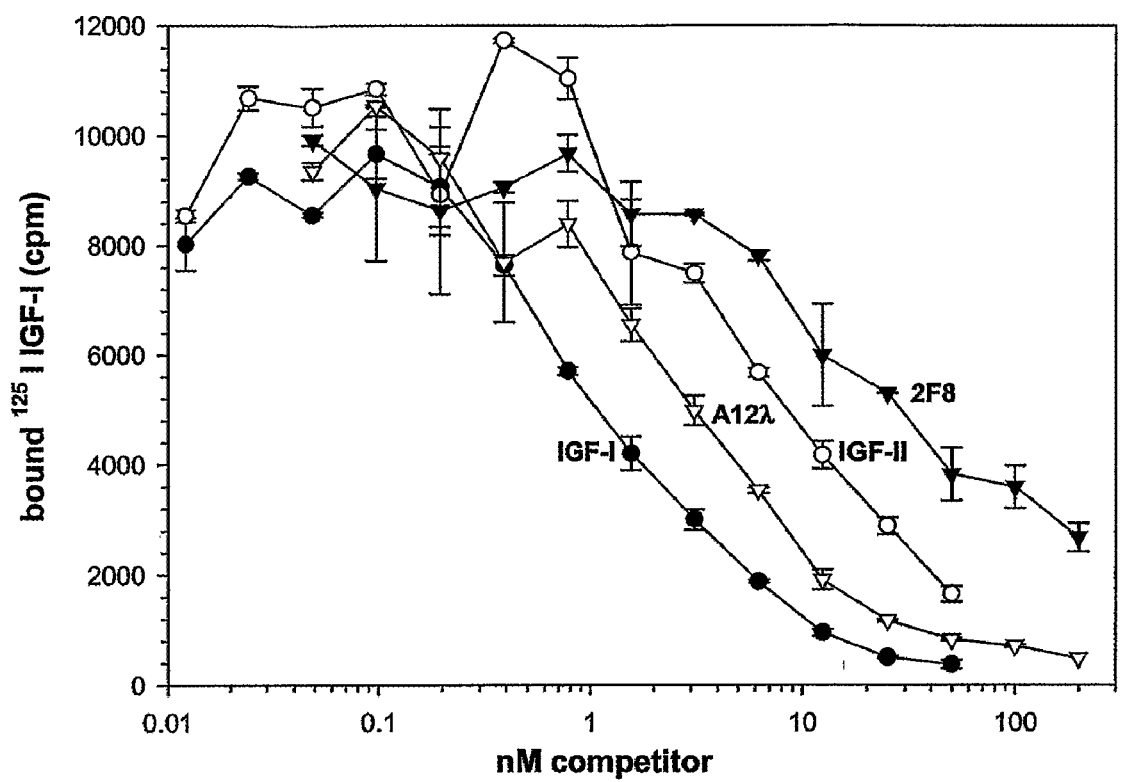
FIG. 16 shows results of an assay that measures the capacity of antibodies 2F8 and A12 (lambda light chain) to block binding of IGF-I to MCF7 cells.

The anti-IGF-IR antibodies were then tested for blocking of radiolabeled ligand to native IGF-IR on human tumor cells. Assay conditions were performed according to Arteaga and Osborne (*Cancer Res.* 49:6237-41 (1989)), with minor modifications. MCF7 human breast cancer cells were seeded into 24 well dishes, and cultured overnight. Sub-confluent monolayers were washed 2-3 times in binding buffer (Iscove's Medium/0.1% BSA) and antibody added in binding buffer. After a short incubation with the antibody at room temperature, 40 pM $^{125}$I-IGF-I (approximately 40,000 cpm/well) was added to each well and incubated for an additional hour with gentle agitation. The wells were then washed three times with ice-cold PBS/0.1% BSA. Monolayers were then lysed with 200 µl 0.5N NaOH and counted in a gamma counter. The results are shown graphically in FIG. 16. On human tumor cells, antibody A12 inhibited ligand binding to IGF-IR with an IC$_{50}$ of 3 nM (0.45 µg/ml). This was slightly lower than the inhibitory activity of cold IGF-I ligand (IC$_{50}$=1 nM), but better than the inhibitory activity of cold IGF-II (IC$_{50}$=9 nM). The differences observed for the two IGF ligands can likely be attributed to the slower binding kinetics of IGF-II for the IGF-IR than ligand IGF-I (Jansson et al., *J. Biol. Chem.* 272:8189-97 (1997). The IC$_{50}$ for antibody 2F8 was determined to be 30 nM (4.5 µg/ml). We subsequently determined the IGF-I ligand blocking activity of the A12 antibody on several different human tumor types. The results are shown in Table 4. Antibody A12 was effective in binding to endogenous cellular IGF-IR and inhibiting ligand binding to a range of human tumor types including cell lines from breast, pancreatic, and colorectal tissue.

TABLE 4

Inhibitory activity of antibody A12 on IGF-I binding to different human tumor types

| Cell line | Cell type | Blocking IC$_{50}$ |
|---|---|---|
| MCF7 | breast | 3 nM |
| T47D | breast | 6 nM |
| OV90 | ovarian | 6 nM |
| BXPC3 | pancreatic | 20 nM |
| HPAC | pancreatic | 10 nM |
| HT-29 | colorectal | 10 nM |
| SK-ES1 | Ewing sarcoma | 2 nM |
| 8226 | myeloma | 20 nM |

Figure 17:
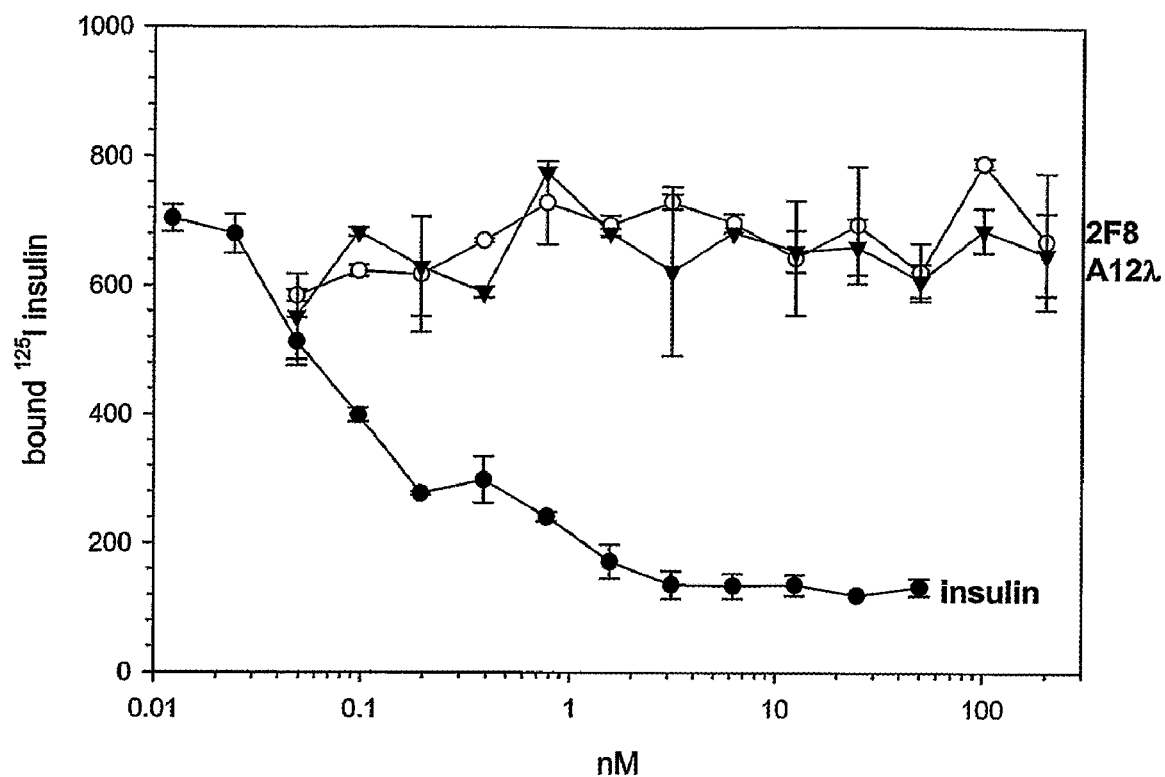
FIG. 17 shows results of an assay that measures the capacity of antibodies 2F8 and A12 to block insulin binding to ZR75-I cells.

The IGF-IR shares considerable homology with the insulin receptor (IR). To determine if the anti-IGF-IR antibodies were specific to this IGF-IR and did not block insulin binding, a cell-based blocking assay was performed on human ZR-75I breast cancer cells. Because insulin can bind to IGF-IR, albeit at three orders of magnitude lower affinity than for the IR, we utilized the human breast cancer line ZR-75I that possesses a higher IR to IGF-IR ratio in comparison to MCF7 cells. By using this line, we reasoned that insulin binding to the cells would be more indicative of specific IR binding. The assay was performed as described above for MCF7 cells and the results shown in FIG. 17. Although cold insulin was able to titrate the binding of radiolabeled insulin to cells, neither 2F8 nor the high affinity A12 antibody blocked insulin binding, even at a concentration of 200 nM antibody, consistent with selective binding of these antibodies to IGF-IR and not IR.

Antibody-Mediated Inhibition of Ligand-Dependent Cell Mitogenesis.

Figure 18A:
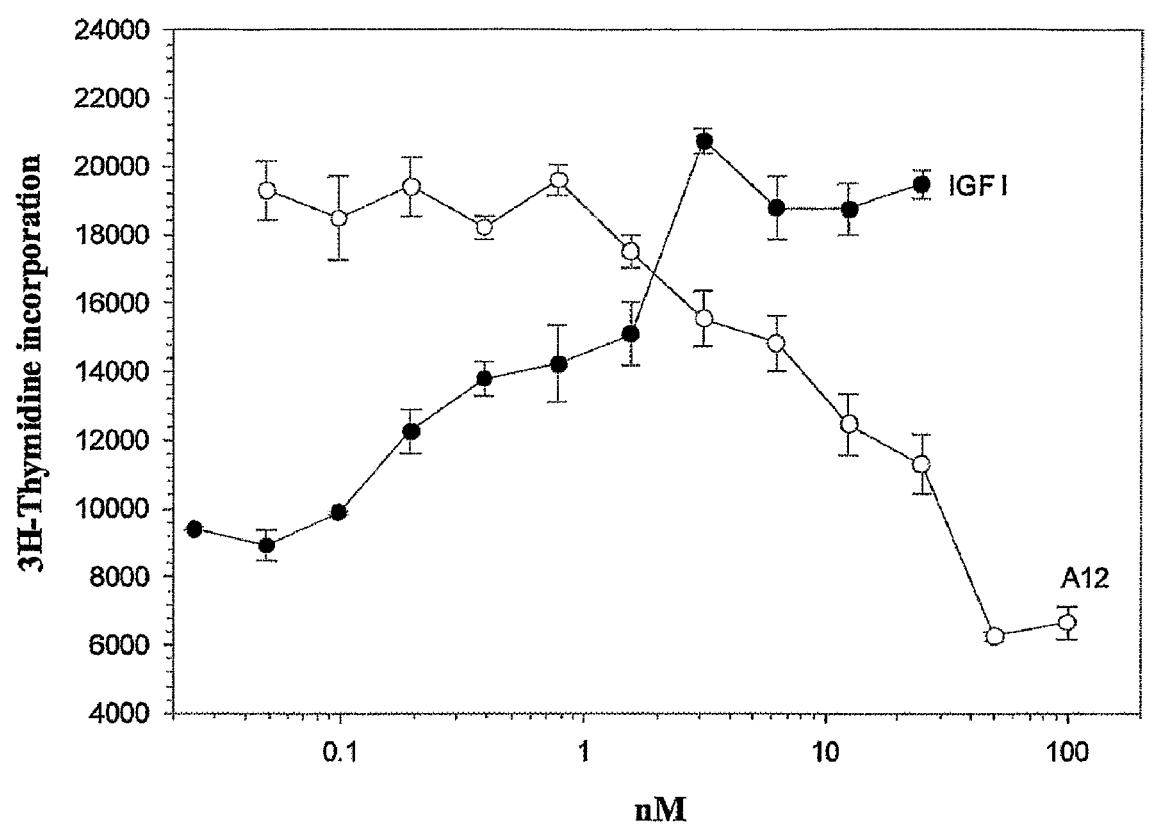
FIG. 18A: MCF7 breast cancer cells.
Figure 18B:
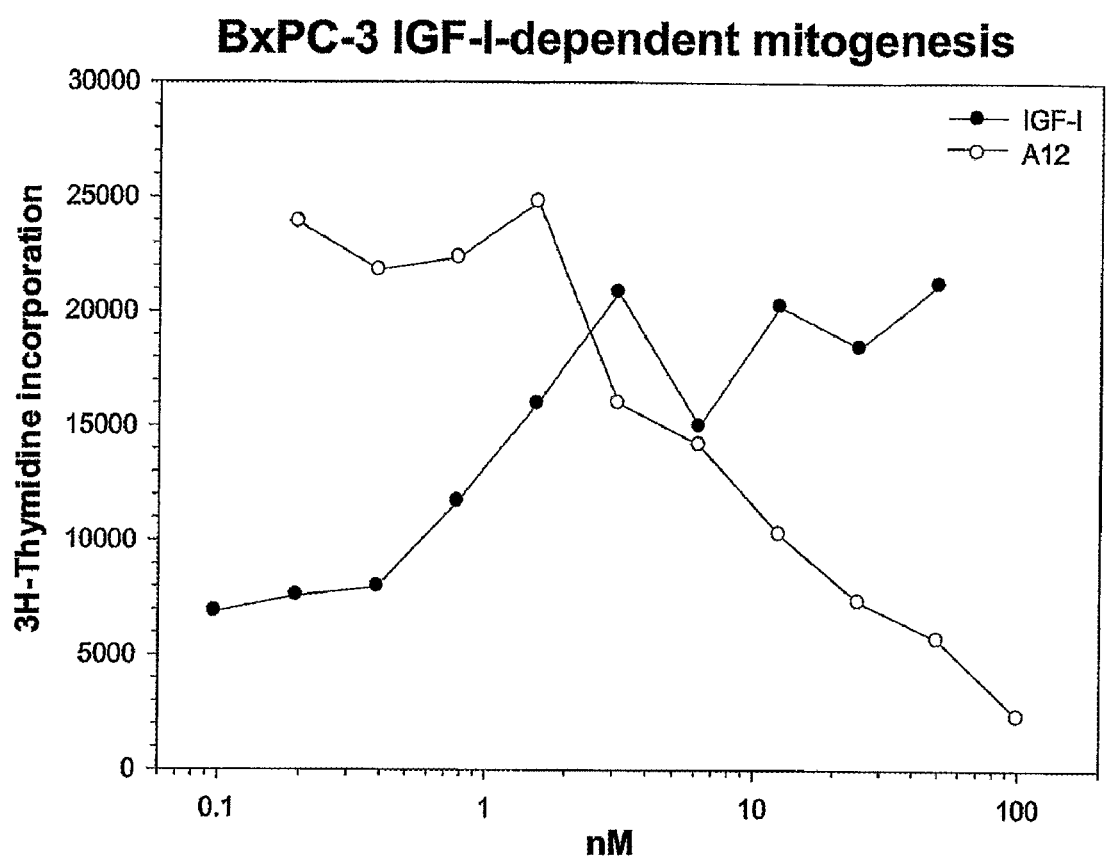
FIG. 18B: BxPC-3 pancreatic cancer cells.
Figure 18C:
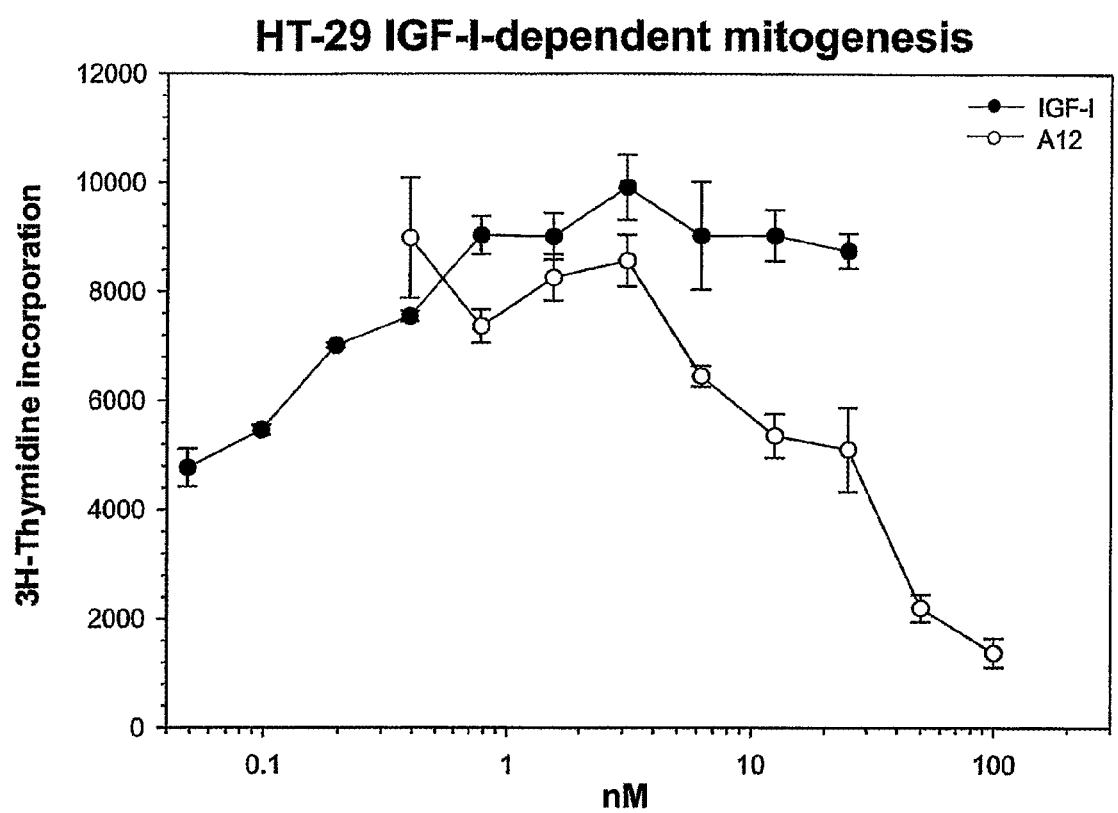
FIG. 18C: HT-29 colon cancer cells.

In order to determine if blocking of IGF-I binding to IGF-IR inhibited cellular proliferation, a mitogenic assay was performed on MCF7 breast cancer cells, BxPC-3 pancreatic cancer cells and HT-29 colon cancer cells. The assay was performed according to Prager, et al. (*Proc. Natl. Acad. Sci. U.S.A.* 91:2181-85 (1994), with some modification. Cells were plated into 96-well tissue culture plates at 5000-10000 cells/well and allowed to adhere overnight. The medium was then replaced with serum free defined medium and incubated overnight at 37° C. Cells were then incubated with IGF-I with or without antibody A12 and incubated overnight at 37° C. 0.25 µCi [³H]thymidine was then added to each well and incubated for 5 hours at 37° C. The supernatant was aspirated and the cells suspended by trypsinization for 5 minutes. The cells were then collected onto a filter and washed three times with water, using a cell harvester. After drying, the filter was processed for reading in a scintillation counter. The results are shown in FIGS. 18A, B and C (MCF7, BxPC-3 and HT-29 respectively). IGF-I datapoints show titration of the ligand to determine the amount necessary to achieve the maximum mitogenic response. In measuring the activity of antibody A12 on various cancer cell types, IGF-I was added at a concentration of 5 nM and the antibody titered from 200 nM to 0.05 nM. Antibody A12 inhibited MCF7 mitogenesis in response to IGF-I ligand in a dose-dependent fashion, with an IC$_{50}$ of 6 nM.

Antibody A12 was then tested for mitogenic inhibition on several additional human tumor cells lines and the results shown in Table 5. Antibody A12 was effective at inhibiting IGF-I ligand-mediated mitogenesis of a variety of human tumor cell lines, including breast cancer, colorectal cancer, and multiple myeloma.

TABLE 5

Inhibitory activity of antibody A12 on mitogenesis of different human tumor cell lines

| Cell line | Cell type | IC$_{50}$ |
|---|---|---|
| MCF7 | breast | 6 nM |
| T47D | breast | 7 nM |
| BT474 | breast | 5 nM |
| BXPC3 | pancreatic | 2 nM |
| HT-29 | colorectal | 6 nM |
| SK-ES1 | Ewing sarcoma | 10 nM |
| 8226 | myeloma | 5 nM |

Antibody-Mediated Inhibition of IGF-I Directed Receptor Phosphorylation and Downstream Signaling.

To visualize the inhibitory effect of the anti-IGF-IR antibodies on IGF-I signaling, receptor auto-phosphorylation and downstream effector molecule phosphorylation analysis was performed in the presence or absence of antibody A12 or 2F8. The MCF7 human breast cancer cell line was selected for use due to its high IGF-IR density. Cells were plated into 10 cm or 6 well culture dishes and grown to 70-80% confluence. The monolayers were then washed twice in PBS and cultured overnight in serum free defined medium. Anti-IGF-IR antibody was then added in fresh serum-free media (100 nM-10 nM) and incubated cells 30 minutes before addition of ligand (10 nM). Cells were incubated with ligand for 10 minutes, then placed on ice and washed with ice-cold PBS. The cells were lysed by the addition of lysis solution (50 mM Tris-HCl, pH 7.4, 150 mM NaCl, 1% TritonX-100, 1 mM EDTA, 1 mM PMSF, 0.5 mM Na$_3$VO$_4$, 1 µg/ml leupeptin, 1 µg/ml pepstatin, and 1 µg/ml aprotinin) and the cells scraped into a centrifuge tube kept on ice for 15 minutes. The lysate was then clarified by centrifugation at 4° C. Solubilized IGF-IR was then immunoprecipitated (IP) from the lysate. Antibody 3B7 (Santa Cruz) or A12 at 1 µg/ml were incubated with 400 µl of lysate overnight at 4° C. Immune complexes were then precipitated by the addition of ProA-sepharose beads for 2 hours at 4° C., pelleted, and washed 3 times with lysis buffer. IPs bound to the ProA beads were stripped into denaturing gel running buffer. Lysate or IP were processed for denaturing gel electrophoresis and run on a 4-12% acrylamide gel and blotted to nylon or nitrocellulose membrane by western blot according to Towbin et al. (*Biotechnology* 24:145-9 (1992)). Tyrosine phosphorylated protein was detected on the blot using an anti-p-tyrosine antibody (Cell Signaling #9411) and an anti-mouse-HRP secondary antibody. IGF-IR was detected with monoclonal antibody C-20 (Santa Cruz). For Akt phosphorylation, phospho-Akt was detected with antibody #559029 and total Akt with #559028 (BD Pharmingen). For MAPK phosphorylation, phospho-p44/42 was detected with #9101 and total p44/42 with #9102 (Cell Signaling Tech.). Bands were visualized with the ECL reagent on X-ray film.

Figure 19B:
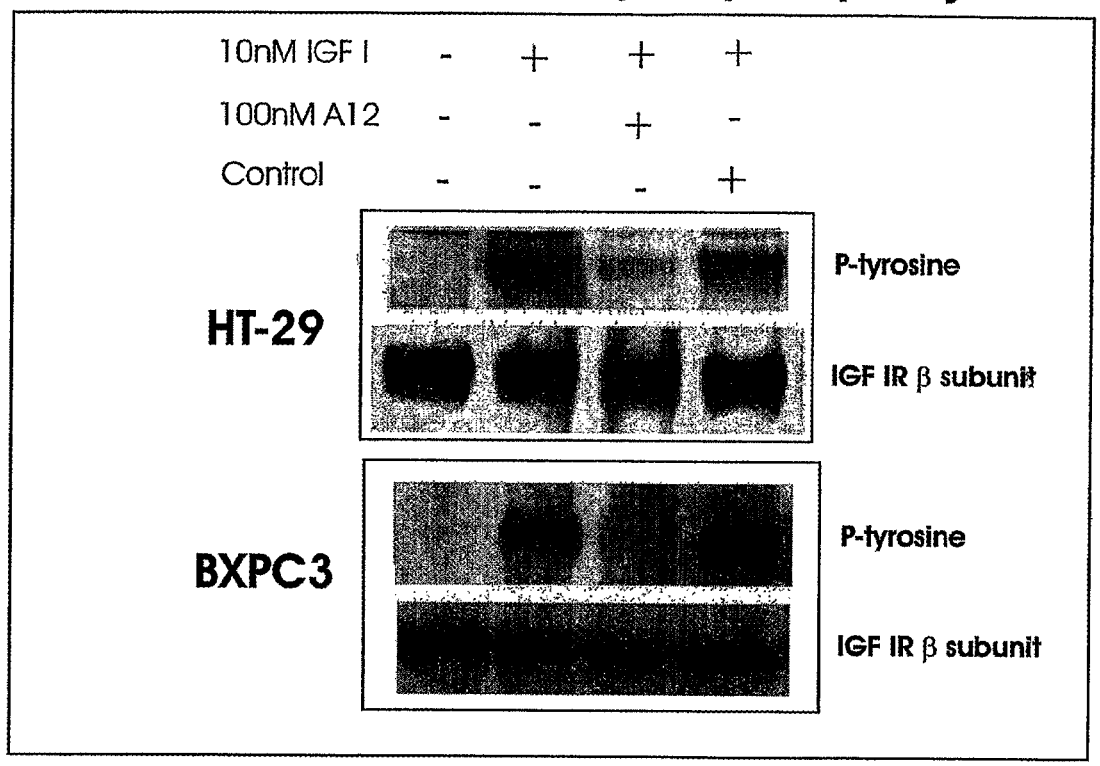
FIG. 19 shows inhibition of IGF-I mediated receptor phosphorylation. Panel A: Inhibition in MCF7 breast cancer cells by antibodies A12 and 2F8. Panel B: Inhibition in HT-29 colorectal cancer cells and BxPC-3 pancreatic cancer cells by antibody A12.

As shown in FIG. 19A, auto-phosphorylation of the IGF-IR in MCF7 cells was arrested following serum deprivation, and the addition of either 2F8 or A12 alone did not induce receptor phosphorylation, thereby demonstrating a lack of detectable agonist activity. Upon the addition of 10 nM IGF-I, IGF-IR phosphorylation was strongly induced. Antibody 2F8 effected an approximately 50% reduction in IGF-IR phosphorylation, whereas the high affinity antibody A12 nearly completely blocked phosphorylation. Similarly, antibody A12 inhibited auto-phosphorylation of IGF-IR in HT-29 colorectal and BxPC-3 pancreatic cancer cells (FIG. 19B).

Downstream effector signaling in response to IGF-I was also inhibited by the anti-IGF-IR antibodies (FIG. 20).

MAPK phosphorylation was considerably inhibited by both 2F8 and A12. Phosphorylation of the anti-apoptotic molecule Akt was less sensitive to anti-IGF-IR antibody blockade with 2F8. It effected only a slight reduction in Akt phosphorylation. A12 significantly inhibited Akt phosphorylation, even at a concentration of 10 nM. Antibody A12 was equally proficient in immunoprecipitating solubilized IGF-IR as the commercial antibody 3B7, but A12 was not capable of detecting denatured IGF-IR immobilized on nylon membranes following western blot transfer.

FACs Binding Analysis of Monoclonal Antibody A12 to Tumor Cell Lines.

Since A12 was capable of immunoprecipitating endogenous IGF-IR, we were therefore interested in determining if A12 could also be used as detection antibody for fluorescence activated cell sorting (FACs). Human tumor cell lines were grown in culture, scraped into ice-cold PBS, and counted. Primary antibody, A12 (0.5 µg), was added to approximately 5 million cells in 250 µl PBS/5% FBS and incubated on ice for 1 hour. The cells were then diluted to 3 mls in PBS/5% FBS, pelleted, and the supernatant aspirated. Secondary phycoerythin (PE)-labeled goat anti-human IgG F(ab)$_2$ fragment was then added in 250 µl PBS/5% FBS at 1:200 and incubated on ice for 60 minutes. Afterwards, the cells were again diluted and pelleted, as before, then resuspended in 500 µl PBS/5% FBS. FACs analysis was then performed on a Epics XL unit (Coulter). As shown in FIG. 21, antibody A12 fully shifted the human breast cancer cell line MCF7 and the human leukemia cell line HEL. IGF-IR negative mouse embryo fibroblasts (R-cells) (obtained from R. Baserga, Thomas Jefferson University, Philadelphia, Pa.) served as the negative control. A12 failed to bind to these cells, indicative of antibody binding specificity for the IGF-IR. A12 did, however, bind and partially shift the mouse tumor cell line Lewis Lung carcinoma, suggesting that this anti-human IGF-IR antibody possesses some cross-reactivity for the mouse IGF-IR.

IGF-I Receptor Internalization Following Binding of Antibody A12.

Figure 22A:
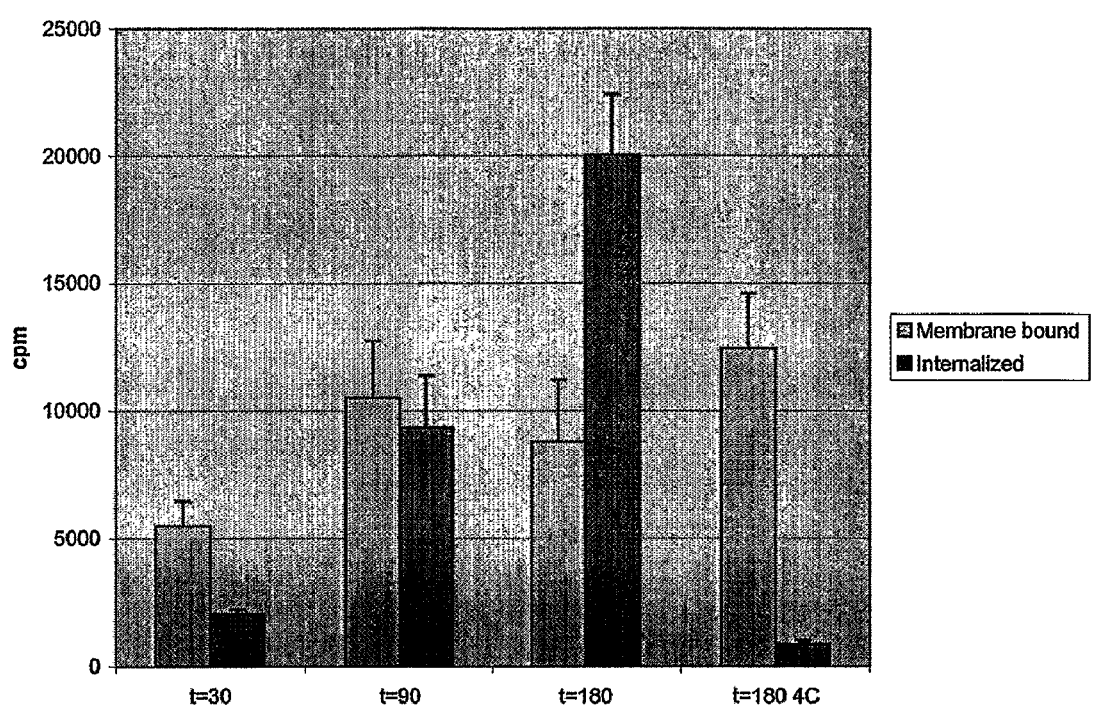
FIG. 22 shows receptor internalization. Panel A shows internalization of labeled antibody A12 following binding to IGF-IR on MCF7 cells. Panel B shows depletion of cell-surface associated IGF-IR. Panel C shows degradation of total cellular IGF-IR after prolonged treatment with A12.

Antibody A12 has been shown to bind native IGF-IR on human tumor cells with high affinity. Antibody A12 was radio-iodinated with $^{125}$iodine using IODO-beads (Pierce) according to manufacturer's instructions. MCF7 human breast cancer cells were plated into 6-well plates and cultured overnight to 50% confluence. One microgram of $^{125}$I-A12 was added to each well and incubated at 37° C. or kept on ice at 4° C. Plates were incubated for 30 minutes, 90 minutes, or 180 minutes and each time point performed in triplicate. The culture at 4° C. was held for 180 minutes. At each time point, wells were washed 1× w/PBS, then stripped for 5 minutes with 100 mM glycine-HCl, 2M urea, pH 2.5. The stripped material, representing membrane bound antibody was kept on ice for counting. Wells were then washed 3 times with PBS and cells solubilized with 1N NaOH/1% TritonX100. The solubilized fraction represented the internalized antibody. Stripped and solubilized fractions were then read on a gamma counter and plotted with standard deviation. As shown in FIG. 22, the level of internalized radioactivity increased with time in the cells cultured at 37° C., while little uptake was observed in cells maintained at 4° C. where membrane transport should be severely retarded. This demonstrated that, upon binding to the IGF-IR, antibody A12 is rapidly internalized, potentially leading to a depletion of surface bound receptor.

Figure 22B:
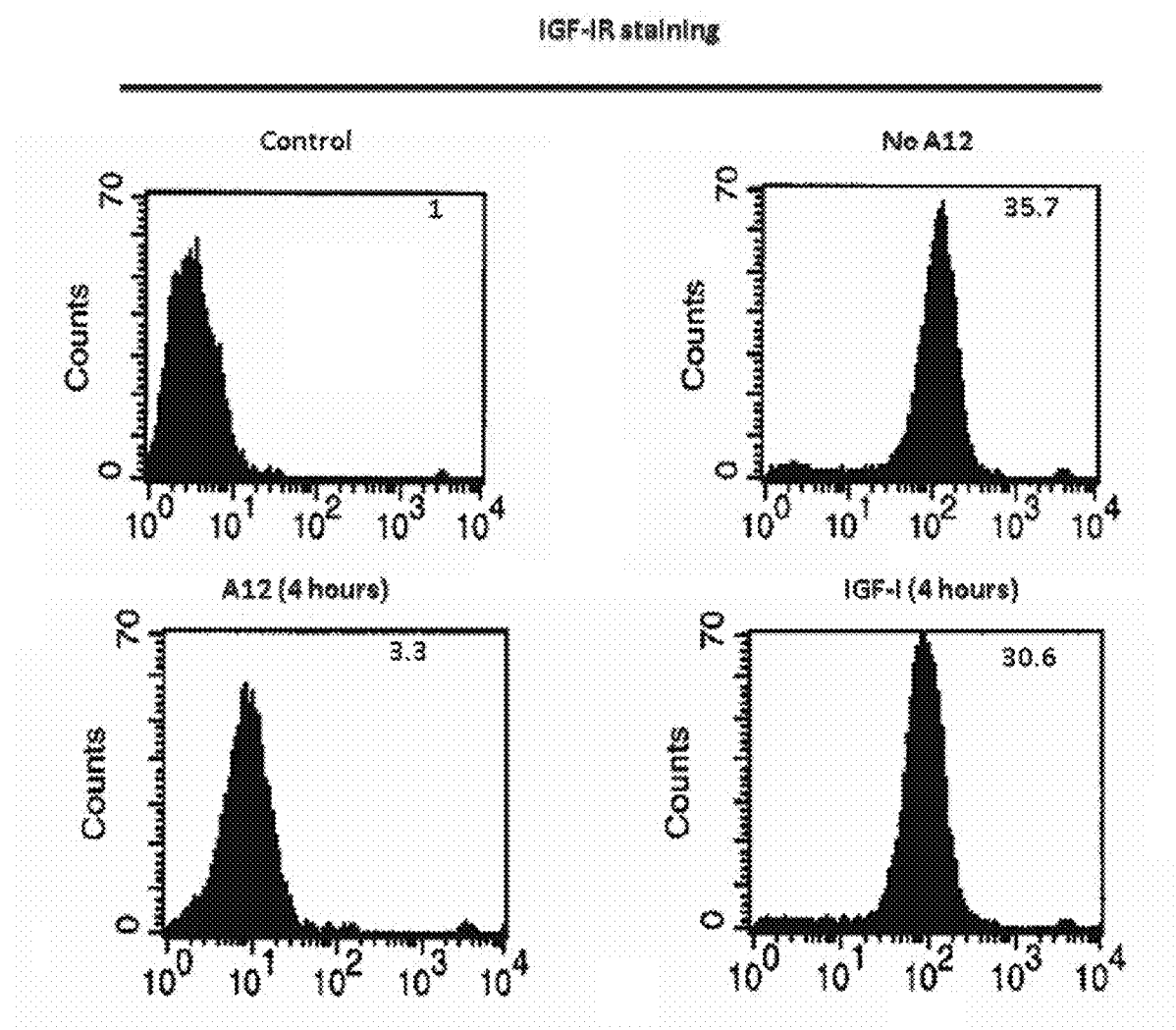
Figure 22C:
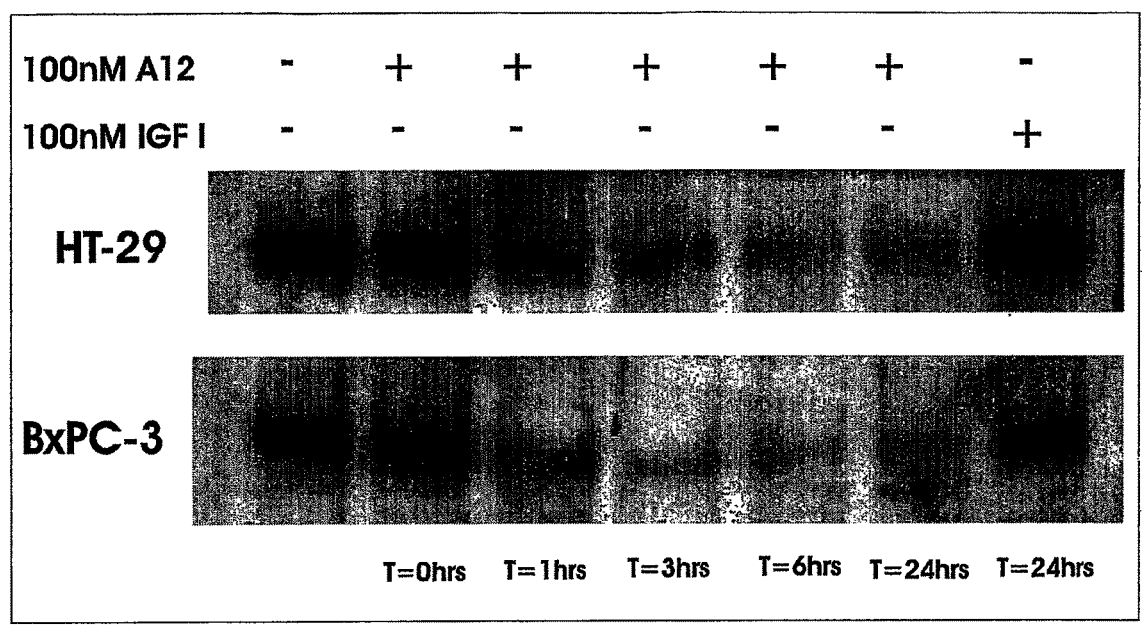

IGF-IR surface receptor density was determined by FACS. Adherent MCF 7 cells were treated for 4 h with 50 nM of antibody A12 of IGF-I at 37° C. Cells were washed in ice-cold PBS/5% BSA twice, and 1×10$^6$ cells were aliquoted to staining tubes and placed on ice. An IGF-IR alpha-polypeptide specific, non-blocking mouse monoclonal antibody (Ab-1, NeoMarkers, Fremont, Calif.), was then incubated with cells at 4° C. for 2 h. After PBS/BSA washes, cells were incubated with anti-mouse IgG phycoerythrin-conjugated secondary antibody (PharMingen, BD Biosciences) for 1 h on ice. After PBS/BSA wash, cells were analyzed by fluorescence-activated cell-sorting assay using a FACSvantage SE flow cytometer (BD Bioscience). As shown in FIG. 22*b*, exposure to A12 resulted in a significant reduction in the fluorescence intensity of MCF7 cells, indicative of surface receptor down-modulation due to internalization. Calculated mean fluorescence intensity ratio indicated a reduction in IGF-IR surface staining of 90% after incubation with A12. This shift was not seen when cells were incubated with A12 at 4° C., consistent with an energy-dependent, antibody-mediated, receptor internalization process. Exposure of cells to IGF-I did not cause a significant change in surface IGF-IR fluorescence intensity, consistent with Western blot analysis showing little effect of ligand on IGF-IR degradation Total cellular IGF-IR was determined HT-29 cells and BxPC-3 cells in response to treatment with IGF-I or A12. As shown in FIG. 22*c*, addition of IGF-I to growing cultures had no effect on IGF-IR expression. In contrast, addition of antibody A12 resulted in severe depletion of IGF-IR levels in the cells after 3-6 hours.

Growth Inhibition of Human Colorectal Tumors Alone or in Combination with Irinotecan (CPT-11).

Figure 23:
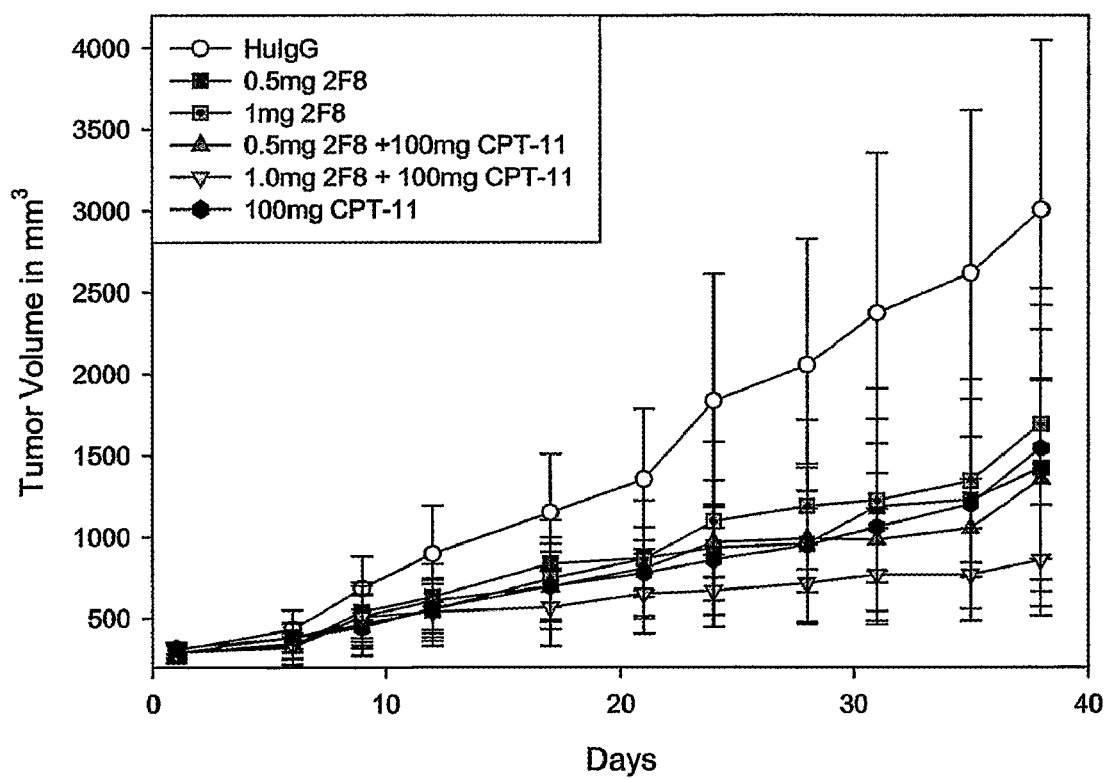
FIG. 23 shows inhibition of HT-29 human colon carcinoma growth in nude mice by antibody 2F8 and CPT-11 (irinotecan) alone or in combination.

We were interested to determine if the anti-IGF-IR antibodies were capable of inhibiting human tumor growth in vivo in a nude mouse xenograft model. Tumors were induced in 3-4 week old athymic nude (nu/nu) mice by subcutaneous injection of 2-3 million viable HT-29 human colorectal cancer cells in cell culture medium. The tumors were allowed to establish and antibody treatment started when the tumor volume reached 200 mm$^3$. Ten animals were injected with tumor cells per treatment group. Antibody was injected intraperitoneally (IP) every three days at 1 mg or 0.5 mg in 0.5 ml TBS. The drug irenotecan (CPT-11) (LKT Laboratories) was injected IP (100 mg/kg) once a week for four weeks from the initiation of antibody treatment. Control animals received a class matched irrelevant human IgG antibody. Tumor measurements were performed at regular intervals using Vernier calipers, measuring height, width, and length and calculated to determine the total tumor volume. The study was terminated when control tumors reached 3000 mm$^3$. As shown in FIG. 23, doses of antibody 2F8 at either 0.5 mg or 1 mg every three days effected a significant inhibition (P<0.05) of tumor growth in this model. There was no statistical difference between the tumor sizes from groups treated with 0.5 or 1 mg 2F8 and the responses were similar to treatment with CPT-11 alone. When 2F8 and CPT-11 were given together the combination resulted in greater inhibition of tumor growth (72% decrease), demonstrating that anti-IGF-IR therapy could enhance the anti-tumor activity of the chemotherapeutic agent CPT-11 on tumor growth.

Anti-Tumor Activity of Antibody A12 on Human Colorectal Tumors In Vivo.

Figure 24:
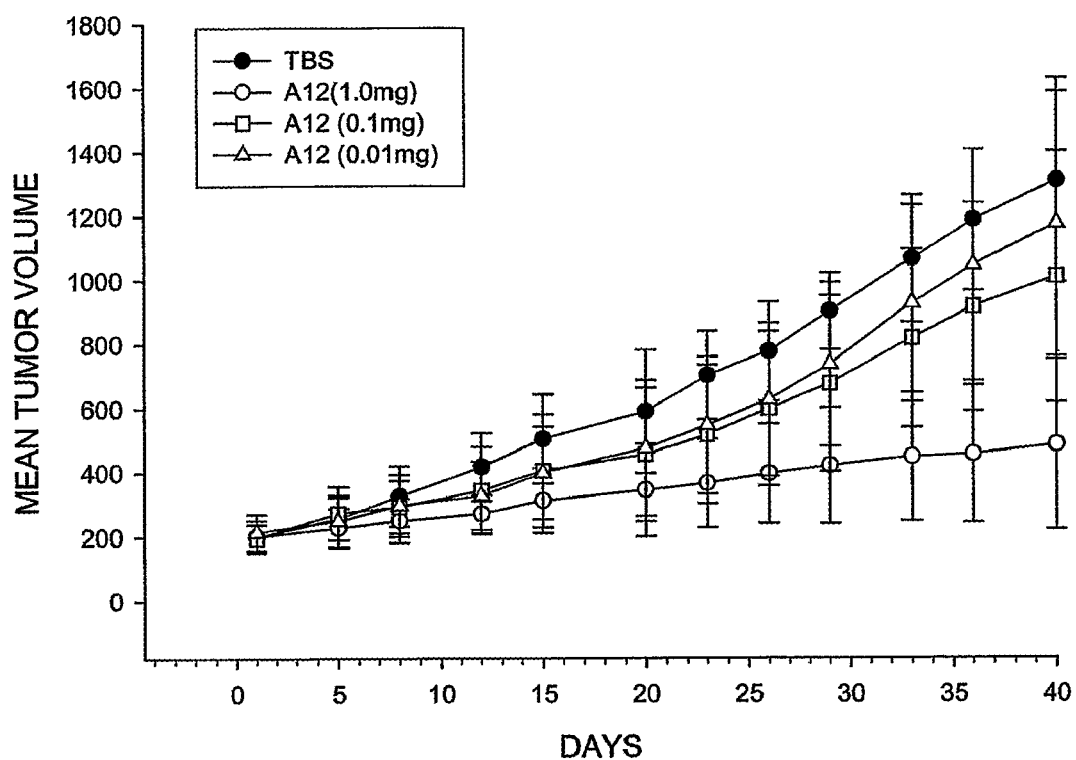
FIG. 24 shows the effect of antibody A12 on HT-29 human colorectal tumor growth in nude mice.

Antibody A12 possesses a 10-fold higher affinity for the IGF-IR than antibody 2F8. Since significant tumor inhibition was observed in vivo with antibody 2F8, we investigated the activity of A12 on the growth of the human colorectal cancer line HT-29 in a mouse xenograft model. Tumors were induced as previously described, and antibody treatment initiated once tumors were established (200 mm$^3$ size). Antibody treatment was then given at a concentration of 1 mg, 100 µg, or 10 µg every three days throughout the duration of the experiment. Ten animals were used per treatment group and control animals received a class match IgG control antibody. As shown in FIG. 24, antibody A12 effected a 74% reduction in tumor growth compared to control (P<0.05). This demonstrated that A12 was effective as a single therapeutic at inhibiting colorectal tumor growth in this xenograft model. A clear dose-response effect was noted in this experiment. Anti-tumor activity was also observed with a dose of 100 µg A12.

Activity of Antibody A12 on Human Breast Cancer In Vivo in a Xenograft Tumor Model.

Figure 25:
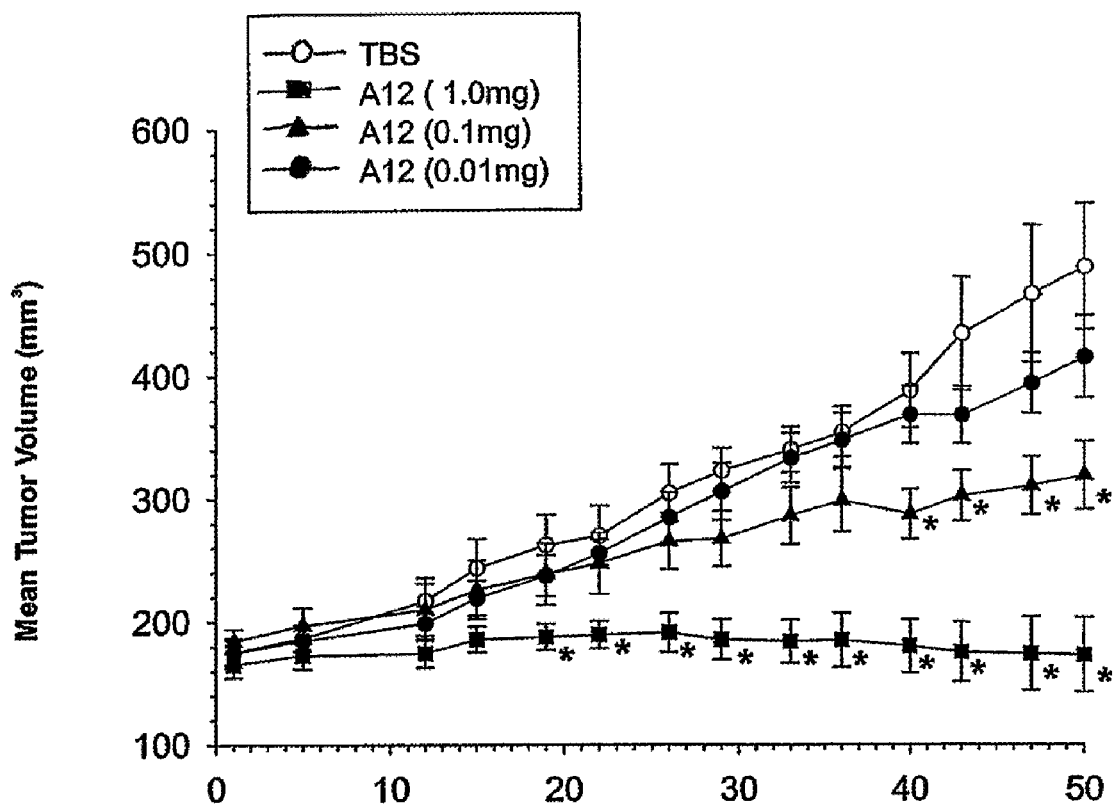
FIG. 25 shows the effect of antibody A12 on MCF7 human breast cancer growth in nude mice.

Antibody A12 exhibited strong inhibitory activity on the IGF-dependent mitogenic stimulation and proliferation of MCF7 cells in vitro. In order to assess its activity on MCF7 tumor growth in vivo, a mouse xenograft tumor model was utilized. MCF7 cells were originally isolated from an estrogen-dependent human tumor and require exogenously added estrogen for maintenance and growth in vivo. Nude mice were implanted with biodegradable estrogen pellets (0.72 mg 17-β-estradiol/pellet, 60 day release). In addition, at the time of subcutaneous tumor cell injection, the mice were also injected in the right flank subcutaneously with 0.5 mg of estradiol in a 50 µl suspension of sesame seed oil. Tumors were allowed to establish a size of approximately 150 mm$^3$ before antibody treatment was initiated. Antibody was injected at 1 mg, 100 µg, and 10 µg doses every three days and continued for the duration of the experiment. At 29 days, treatment of animals with 1 mg of A12 effected an 89% reduction in tumor growth (FIG. 25). Minimal growth was apparent for the established tumors in this treatment group. A dose dependent response was noted for A12 treatments in this model. The study demonstrated that A12 was effective in significantly reducing the growth of a human breast cancer cell line in vivo. Further, treating with antibody alone at 1 mg/dose, tumor regression was observed and continued to the termination of the study (50 days).

Efficacy of A12 in Combination with CPT-11 or Gemcitabine in BxPC-3 Pancreatic Carcinoma Xenografts Athymic nu/nu mice were injected subcutaneously with 2×10$^6$ BxPC-3 human pancreatic carcinoma cells mixed 1:1 with Matrigel. Twenty days later, when tumors reached 200-300 mm$^3$, mice were randomized and divided into treatment groups: 1) TBS control; 2) mAb A12 at 1 mg/dose, 3 times per week; 3) 1 mg irinotecan, once every 7 days; 4) mAb A12+irinotecan; 5) 2.5 mg gemcitabine, once every 7 days; 6) mAb A12+gemcitabine. All treatments were administered by intraperitoneal injection. Tumor measurements were recorded twice weekly using the formula Volume=(π/6)l×w$^2$.

At day 18 three animals per group were sacrificed and the tumors resected for midpoint histological evaluation. Treatment and tumor measurements continued on the remaining animals until day 44 with the exception of the TBS group. This control group was sacrificed at day 37 due to tumor ulceration and necrosis. At termination of the study final tumor measurements were recorded, animals sacrificed, and four per group had tumors resected for endpoint histological evaluation.

Figure 26:
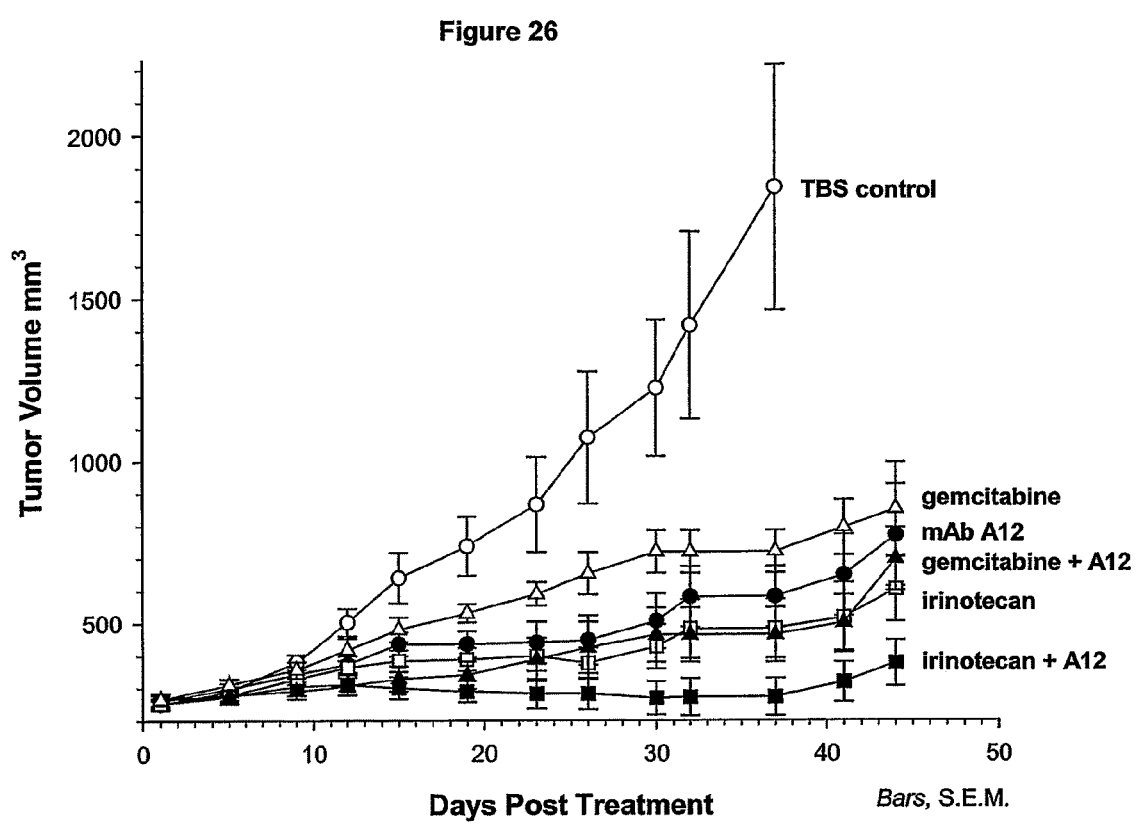
FIG. 26 shows inhibition of BxPC-3 pancreatic cancer xenografts in nude mice by antibody A12, gemcitabine, or CPT-11 (irinotecan) alone, or in combination.

BxPC-3 tumors were very responsive to mAb A12, and 2 of eight animals had partial tumor regressions after five weeks of treatment. The response of BxPC-3 tumors to irinotecan or gemcitabine alone was comparable to the antibody, but there were no tumor regressions. Antibody A12, when combined with irinotecan or gemcitabine was more effective than any agent alone (FIG. 26), with irinotecan+Mab A12 being the more effective combination. For combined A12 and irinotecan, three of nine animals had partial tumor regressions. However, there were no tumor regressions among the animals given irinotecan. (Table 5).

TABLE 5

Inhibition of Growth of BxPC-3 Xenografts

| Day | mAb A12 | | Irinotecan | | mAb A12 + Irinotecan | | Gemcitabine | | mAb A12 + Gemcitabine | |
|---|---|---|---|---|---|---|---|---|---|---|
| | T/C % | Regressions* | T/C % | Regressions | T/C % | Regressions | T/C % | Regressions | T/C % | Regressions |
| 19 | 57 | 2/12 | 52 | 0/12 | 40 | 3/12 | 68 | 0/11 | 44 | 0/12 |
| 23 | 49 | 2/9 | 45 | 0/8 | 32 | 3/9 | 65 | 0/8 | 42 | 1/9 |
| 26 | 40 | 2/9 | 35 | 0/8 | 26 | 3/9 | 58 | 0/8 | 37 | 1/9 |
| 30 | 40 | 2/8 | 34 | 0/8 | 22 | 3/9 | 56 | 0/8 | 36 | 1/9 |
| 32 | 39 | 2/8 | 34 | 0/8 | 19 | 3/9 | 48 | 0/8 | 31 | 1/9 |
| 37 | 30 | 2/8 | 26 | 0/8 | 15 | 3/9 | 37 | 0/8 | 24 | 1/9 |
| 41 | — | 2/8 | — | 0/7 | — | 3/8 | | 0/8 | — | 1/8 |
| 44 | — | 2/8 | — | 0/7 | — | 3/8 | | 0/7 | — | 0/6 |

T/C % is tumor growth inhibition relative to control
*Regressions defined as individual tumor volumes < day 1 of treatment.

Efficacy of A12 in Combination with CPT-11 or Paclitaxel in HT-29 Colorectal Cancer Xenografts Female thymic nu/nu mice were injected subcutaneously with HT-29 human colon carcinoma cell suspension, at 5×10$^6$ cells in 0.4 ml mixed 1:1 with Matrigel. When tumors reached ~200 mm$^3$ mice were randomized and divided into treatment groups: 1) TBS control; 2) mAb A12 at 1 mg/dose, 3 times per week; 3) 2 mg irinotecan, once every 7 days; 4) mAb A12+irinotecan; 5) 121 µg paclitaxel in 0.2 ml, once every 7 days; 6) mAb A12+paclitaxel. All treatments were administered by intraperitoneal injection.

Treatment continued for six weeks and tumor measurements were recorded twice weekly using the formula Volume=(π/6)l×w$^2$. At day 21 four animals per group were sacrificed and the tumors resected for histological evaluation. Treatment and tumor measurements continued on the remaining animals until day 40. At that time final tumor measurements were recorded, animals sacrificed, and four per group had tumor resected for endpoint histological evaluation.

Figure 27:
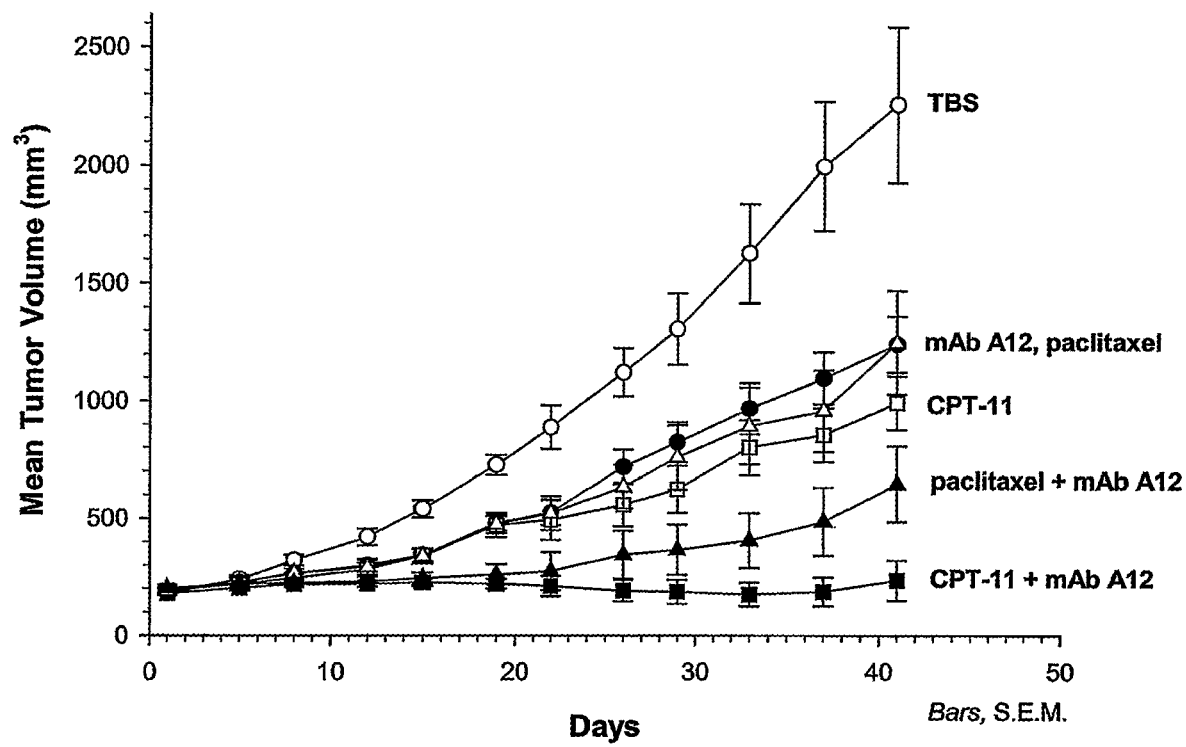
FIG. 27 shows inhibition of HT-29 colorectal cancer xenografts in nude mice by antibody A12, paclitaxel, or CPT-11 (irinotecan) alone, or in combination.

Single-agent mAb A12, CPT-11, or paclitaxel significantly (P<0.02) inhibited the growth of HT-29 xenografts compared to the TBS control group (FIG. 27). Combination therapy of mAb A12 with either CPT-11 or paclitaxel showed a significant inhibition (P<0.003) in tumor growth compared to either treatment alone.

No tumor regressions were observed in the single-therapy groups. Control tumors in situ appeared highly vascularized at day 22 as did single-therapy groups at day 40. However, combination therapy with CPT-11+mAb A12 resulted in partial tumor regressions in six out of eight animals, and combination therapy with paclitaxel and mAb A12 resulted in regressions in three of eight animals.

TABLE 6

Inhibition of Growth of HT-29 Xenografts

| Day | mAb A12 T/C % | CPT-11 T/C % | paclitaxel T/C % | A12 + CPT-11 | | A12 + paclitaxel | |
|---|---|---|---|---|---|---|---|
| | | | | T/C % | Regressions* | T/C % | Regressions |
| 12 | 69 | 63 | 66 | 52 | 0/12 | 48 | 1/12 |
| 15 | 62 | 59 | 59 | 42 | 0/12 | 40 | 3/12 |
| 19 | 64 | 61 | 62 | 30 | 3/12 | 32 | 5/12 |
| 22 | 58 | 52 | 56 | 24 | 4/8 | 28 | 4/8 |
| 26 | 62 | 47 | 54 | 17 | 6/8 | 27 | 3/8 |
| 29 | 61 | 45 | 55 | 14 | 6/8 | 24 | 3/8 |
| 33 | 58 | 40 | 52 | 11 | 5/8 | 22 | 3/8 |
| 36 | 53 | 40 | 45 | 9 | 5/8 | 22 | 2/8 |
| 40 | 54 | 41 | 52 | 10 | 2/6 | 26 | 2/8 |

T/C % is tumor growth inhibition relative to control
*Regressions defined as individual tumor volumes < day 1 of treatment.

It is understood and expected that variations in the principles of invention herein disclosed may be made by one skilled in the art and it is intended that such modifications are to be included within the scope of the present invention.

What is claimed is:

1. A method of reducing tumor growth which comprises administering to a mammal an effective amount of the human antibody comprising the heavy chain variable domain of SEQ ID NO:2 and the light chain variable domain of SEQ ID NO:6.

2. The method of claim 1, which further comprises administering an effective amount of an anti-neoplastic agent.

3. The method of claim 2, wherein the anti-neoplastic agent is an inhibitor of topoisomerase I or topoisomerase II.

4. The method of claim 3, wherein the anti-neoplastic agent is selected from the group consisting of irinotecan, camptothecan, and etoposide.

5. The method of claim 1, which further comprises administering an effective amount of an EGFR antagonist.

6. The method of claim 5, wherein the EGFR antagonist is an antibody.

7. A method of promoting tumor regression which comprises administering to a mammal an effective amount of the human antibody comprising the heavy chain variable domain of SEQ ID NO:2 and the light chain variable domain of SEQ ID NO:6.

8. The method of claim 7, which further comprises administering an effective amount of an anti-neoplastic agent.

9. The method of claim 8, wherein the anti-neoplastic agent is an inhibitor of topoisomerase I or topoisomerase II.

10. The method of claim 9, wherein the anti-neoplastic agent is selected from the group consisting of irinotecan, camptothecan, and etoposide.

11. The method of claim 7, which further comprises administering an effective amount of an EGFR antagonist.

12. The method of claim 11, wherein the EGFR antagonist is an antibody.

13. The method of claim 1, wherein the tumor is a breast tumor, colorectal tumor, pancreatic tumor, ovarian tumor, lung tumor, prostate tumor, bone or soft tissue sarcoma or myeloma.

14. The method of claim 7, wherein the tumor is a breast tumor, colorectal tumor, pancreatic tumor, ovarian tumor, lung tumor, prostate tumor, bone or soft tissue sarcoma or myeloma.

* * * * *

UNITED STATES PATENT AND TRADEMARK OFFICE
CERTIFICATE OF CORRECTION

| | |
|---|---|
| PATENT NO. | : 7,968,093 B2 |
| APPLICATION NO. | : 12/640671 |
| DATED | : June 28, 2011 |
| INVENTOR(S) | : Dale L. Ludwig |

Page 1 of 1

It is certified that error appears in the above-identified patent and that said Letters Patent is hereby corrected as shown below:

Bibliography page, Column 2, (57) Abstract, line 8, delete "ant-" and insert --anti--, therefor.

Column 55, lines 24-25, delete "camptothecan" and insert --camptothecin--, therefor.

Column 56, line 19, delete "camptothecan" and insert --camptothecin--, therefor.

Signed and Sealed this
Sixteenth Day of August, 2011

David J. Kappos
*Director of the United States Patent and Trademark Office*

```
                         SEQUENCE LISTING

<160> NUMBER OF SEQ ID NOS: 33

<210> SEQ ID NO 1
<211> LENGTH: 390
<212> TYPE: DNA
<213> ORGANISM: Homo sapiens

<400> SEQUENCE: 1 gag gtc cag ctg gtg cag tct ggg gct gag gtg aag aag cct ggg tcc        48
Glu Val Gln Leu Val Gln Ser Gly Ala Glu Val Lys Lys Pro Gly Ser
  1               5                  10                  15 tcg gtg aag gtc tcc tgc aag gct tct gga ggc acc ttc agc agc tat        96
Ser Val Lys Val Ser Cys Lys Ala Ser Gly Gly Thr Phe Ser Ser Tyr
             20                  25                  30 gct atc agc tgg gtg cga cag gcc cct gga caa ggg ctt gag tgg atg       144
Ala Ile Ser Trp Val Arg Gln Ala Pro Gly Gln Gly Leu Glu Trp Met
         35                  40                  45 gga ggg atc atc cct atc ttt ggt aca gca aac tac gca cag aag ttc       192
Gly Gly Ile Ile Pro Ile Phe Gly Thr Ala Asn Tyr Ala Gln Lys Phe
     50                  55                  60 cag ggc aga gtc acg att acc gcg gac aaa tcc acg agc aca gcc tac       240
Gln Gly Arg Val Thr Ile Thr Ala Asp Lys Ser Thr Ser Thr Ala Tyr
 65                  70                  75                  80 atg gag ctg agc agc ctg aga tct gag gac acg gcc gtg tat tac tgt       288
Met Glu Leu Ser Ser Leu Arg Ser Glu Asp Thr Ala Val Tyr Tyr Cys
                 85                  90                  95 gcg aga gcg cca tta cga ttt ttg gag tgg tcc acc caa gac cac tac       336
Ala Arg Ala Pro Leu Arg Phe Leu Glu Trp Ser Thr Gln Asp His Tyr
            100                 105                 110 tac tac tac tac atg gac gtc tgg ggc aaa ggg acc acg gtc acc gtc       384
Tyr Tyr Tyr Tyr Met Asp Val Trp Gly Lys Gly Thr Thr Val Thr Val
        115                 120                 125 tca agc                                                               390
Ser Ser
    130

<210> SEQ ID NO 2
<211> LENGTH: 130
<212> TYPE: PRT
<213> ORGANISM: Homo sapiens
```

<400> SEQUENCE: 2

```
Glu Val Gln Leu Val Gln Ser Gly Ala Glu Val Lys Lys Pro Gly Ser
                 5                  10                  15
Ser Val Lys Val Ser Cys Lys Ala Ser Gly Gly Thr Phe Ser Ser Tyr
             20                  25                  30
Ala Ile Ser Trp Val Arg Gln Ala Pro Gly Gln Gly Leu Glu Trp Met
         35                  40                  45
Gly Gly Ile Ile Pro Ile Phe Gly Thr Ala Asn Tyr Ala Gln Lys Phe
     50                  55                  60
Gln Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ala Pro Leu Arg Phe Leu Glu Trp Ser Thr Gln Asp His Tyr
            100                 105                 110
Tyr Tyr Tyr Tyr Met Asp Val Trp Gly Lys Gly Thr Thr Val Thr Val
        115                 120                 125
Ser Ser
130
```

<210> SEQ ID NO 3
<211> LENGTH: 1440
<212> TYPE: DNA
<213> ORGANISM: Homo sapiens

<400> SEQUENCE: 3

```
atg gga tgg tca tgt atc atc ctt ttt cta gta gca act gca act gga        48
Met Gly Trp Ser Cys Ile Ile Leu Phe Leu Val Ala Thr Ala Thr Gly
                 5                  10                  15 gta cat tca gag gtc cag ctg gtg cag tct ggg gct gag gtg aag aag        96
Val His Ser Glu Val Gln Leu Val Gln Ser Gly Ala Glu Val Lys Lys
             20                  25                  30 cct ggg tcc tcg gtg aag gtc tcc tgc aag gct tct gga ggc acc ttc       144
Pro Gly Ser Ser Val Lys Val Ser Cys Lys Ala Ser Gly Gly Thr Phe
         35                  40                  45 agc agc tat gct atc agc tgg gtg cga cag gcc cct gga caa ggg ctt       192
Ser Ser Tyr Ala Ile Ser Trp Val Arg Gln Ala Pro Gly Gln Gly Leu
     50                  55                  60 gag tgg atg gga ggg atc atc cct atc ttt ggt aca gca aac tac gca       240
Glu Trp Met Gly Gly Ile Ile Pro Ile Phe Gly Thr Ala Asn Tyr Ala
 65                  70                  75                  80 cag aag ttc cag ggc aga gtc acg att acc gcg gac aaa tcc acg agc       288
Gln Lys Phe Gln Gly Arg Val Thr Ile Thr Ala Asp Lys Ser Thr Ser
                 85                  90                  95 aca gcc tac atg gag ctg agc agc ctg aga tct gag gac acg gcc gtg       336
Thr Ala Tyr Met Glu Leu Ser Ser Leu Arg Ser Glu Asp Thr Ala Val
            100                 105                 110 tat tac tgt gcg aga gcg cca tta cga ttt ttg gag tgg tcc acc caa       384
Tyr Tyr Cys Ala Arg Ala Pro Leu Arg Phe Leu Glu Trp Ser Thr Gln
        115                 120                 125 gac cac tac tac tac tac atg gac gtc tgg ggc aaa ggg acc acg            432
Asp His Tyr Tyr Tyr Tyr Tyr Met Asp Val Trp Gly Lys Gly Thr Thr
    130                 135                 140 gtc acc gtc tca agc gcc tcc acc aag ggc cca tcg gtc ttc ccc ctg       480
Val Thr Val Ser Ser Ala Ser Thr Lys Gly Pro Ser Val Phe Pro Leu
145                 150                 155                 160 gca ccc tcc tcc aag agc acc tct ggg ggc aca gcg gcc ctg ggc tgc       528
Ala Pro Ser Ser Lys Ser Thr Ser Gly Gly Thr Ala Ala Leu Gly Cys
                165                 170                 175
```

```
ctg gtc aag gac tac ttc ccc gaa ccg gtg acg gtg tcg tgg aac tca      576
Leu Val Lys Asp Tyr Phe Pro Glu Pro Val Thr Val Ser Trp Asn Ser
        180                 185                 190 ggc gcc ctg acc agc ggc gtg cac acc ttc ccg gct gtc cta cag tcc      624
Gly Ala Leu Thr Ser Gly Val His Thr Phe Pro Ala Val Leu Gln Ser
            195                 200                 205 tca gga ctc tac tcc ctc agc agc gtg gtg acc gtg ccc tcc agc agc      672
Ser Gly Leu Tyr Ser Leu Ser Ser Val Val Thr Val Pro Ser Ser Ser
    210                 215                 220 ttg ggc acc cag acc tac atc tgc aac gtg aat cac aag ccc agc aac      720
Leu Gly Thr Gln Thr Tyr Ile Cys Asn Val Asn His Lys Pro Ser Asn
225                 230                 235                 240 acc aag gtg gac aag aaa gtt gag ccc aaa tct tgt gac aaa act cac      768
Thr Lys Val Asp Lys Lys Val Glu Pro Lys Ser Cys Asp Lys Thr His
                245                 250                 255 aca tgc cca ccg tgc cca gca cct gaa ctc ctg ggg gga ccg tca gtc      816
Thr Cys Pro Pro Cys Pro Ala Pro Glu Leu Leu Gly Gly Pro Ser Val
            260                 265                 270 ttc ctc ttc ccc cca aaa ccc aag gac acc ctc atg atc tcc cgg acc      864
Phe Leu Phe Pro Pro Lys Pro Lys Asp Thr Leu Met Ile Ser Arg Thr
    275                 280                 285 cct gag gtc aca tgc gtg gtg gtg gac gtg agc cac gaa gac cct gag      912
Pro Glu Val Thr Cys Val Val Val Asp Val Ser His Glu Asp Pro Glu
290                 295                 300 gtc aag ttc aac tgg tac gtg gac ggc gtg gag gtg cat aat gcc aag      960
Val Lys Phe Asn Trp Tyr Val Asp Gly Val Glu Val His Asn Ala Lys
305                 310                 315                 320 aca aag ccg cgg gag gag cag tac aac agc acg tac cgg gtg gtc agc     1008
Thr Lys Pro Arg Glu Glu Gln Tyr Asn Ser Thr Tyr Arg Val Val Ser
                325                 330                 335 gtc ctc acc gtc ctg cac cag gac tgg ctg aat ggc aag gag tac aag     1056
Val Leu Thr Val Leu His Gln Asp Trp Leu Asn Gly Lys Glu Tyr Lys
            340                 345                 350 tgc aag gtc tcc aac aaa gcc ctc cca gcc ccc atc gag aaa acc atc     1104
Cys Lys Val Ser Asn Lys Ala Leu Pro Ala Pro Ile Glu Lys Thr Ile
    355                 360                 365 tcc aaa gcc aaa ggg cag ccc cga gaa cca cag gtg tac acc ctg ccc     1152
Ser Lys Ala Lys Gly Gln Pro Arg Glu Pro Gln Val Tyr Thr Leu Pro
370                 375                 380 cca tcc cgg gag gag atg acc aag aac cag gtc agc ctg acc tgc ctg     1200
Pro Ser Arg Glu Glu Met Thr Lys Asn Gln Val Ser Leu Thr Cys Leu
385                 390                 395                 400 gtc aaa ggc ttc tat ccc agc gac atc gcc gtg gag tgg gag agc aat     1248
Val Lys Gly Phe Tyr Pro Ser Asp Ile Ala Val Glu Trp Glu Ser Asn
                405                 410                 415 ggg cag ccg gag aac aac tac aag acc acg cct ccc gtg ctg gac tcc     1296
Gly Gln Pro Glu Asn Asn Tyr Lys Thr Thr Pro Pro Val Leu Asp Ser
            420                 425                 430 gac ggc tcc ttc ttc ctc tac agc aag ctc acc gtg gac aag agc agg     1344
Asp Gly Ser Phe Phe Leu Tyr Ser Lys Leu Thr Val Asp Lys Ser Arg
    435                 440                 445 tgg cag cag ggg aac gtc ttc tca tgc tcc gtg atg cat gag gct ctg     1392
Trp Gln Gln Gly Asn Val Phe Ser Cys Ser Val Met His Glu Ala Leu
450                 455                 460 cac aac cac tac acg cag aag agc ctc tcc ctg tct ccg ggt aaa tga    1440
His Asn His Tyr Thr Gln Lys Ser Leu Ser Leu Ser Pro Gly Lys
465                 470                 475

<210> SEQ ID NO 4
<211> LENGTH: 479
```

<212> TYPE: PRT
<213> ORGANISM: Homo sapiens

<400> SEQUENCE: 4

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ala Pro Leu Arg Phe Leu Glu Trp Ser Thr Gln
        115                 120                 125

Asp His Tyr Tyr Tyr Tyr Met Asp Val Trp Gly Lys Gly Thr Thr
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
        420                 425                 430

Asp Gly Ser Phe Phe Leu Tyr Ser Lys Leu Thr Val Asp Lys Ser Arg
    435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys
465                 470                 475

<210> SEQ ID NO 5
<211> LENGTH: 327
<212> TYPE: DNA
<213> ORGANISM: Homo sapiens

<400> SEQUENCE: 5 tct tct gag ctg act cag gac cct gct gtg tct gtg gcc ttg gga cag      48
Ser Ser Glu Leu Thr Gln Asp Pro Ala Val Ser Val Ala Leu Gly Gln
                5                   10                  15 aca gtc agg atc aca tgc caa gga gac agc ctc aga agc tat tat gca      96
Thr Val Arg Ile Thr Cys Gln Gly Asp Ser Leu Arg Ser Tyr Tyr Ala
            20                  25                  30 agc tgg tac cag cag aag cca gga cag gcc cct gta ctt gtc atc tat     144
Ser Trp Tyr Gln Gln Lys Pro Gly Gln Ala Pro Val Leu Val Ile Tyr
        35                  40                  45 ggt aaa aac aac cgg ccc tca ggg atc cca gac cga ttc tct ggc tcc     192
Gly Lys Asn Asn Arg Pro Ser Gly Ile Pro Asp Arg Phe Ser Gly Ser
    50                  55                  60 agc tca gga aac aca gct tcc ttg acc atc act ggg gct cag gcg gaa     240
Ser Ser Gly Asn Thr Ala Ser Leu Thr Ile Thr Gly Ala Gln Ala Glu
65                  70                  75                  80 gat gag gct gac tat tac tgt aac tcc cgg gac aac agt gat aac cgt     288
Asp Glu Ala Asp Tyr Tyr Cys Asn Ser Arg Asp Asn Ser Asp Asn Arg
                85                  90                  95 ctg ata ttt ggc ggc ggg acc aag ctg acc gtc ctc agt                 327
Leu Ile Phe Gly Gly Gly Thr Lys Leu Thr Val Leu Ser
                100                 105

<210> SEQ ID NO 6
<211> LENGTH: 109
<212> TYPE: PRT
<213> ORGANISM: Homo sapiens

<400> SEQUENCE: 6

Ser Ser Glu Leu Thr Gln Asp Pro Ala Val Ser Val Ala Leu Gly Gln
                5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Asn Ser Asp Asn Arg
                85                  90                  95

Leu Ile Phe Gly Gly Gly Thr Lys Leu Thr Val Leu Ser
                100                 105

<210> SEQ ID NO 7
<211> LENGTH: 702
<212> TYPE: DNA
<213> ORGANISM: Homo sapiens

<400> SEQUENCE: 7

```
atg gga tgg tca tgt atc atc ctt ttt cta gta gca act gca act gga      48
Met Gly Trp Ser Cys Ile Ile Leu Phe Leu Val Ala Thr Ala Thr Gly
                 5                  10                  15 gta cat tca tct tct gag ctg act cag gac cct gct gtg tct gtg gcc      96
Val His Ser Ser Ser Glu Leu Thr Gln Asp Pro Ala Val Ser Val Ala
             20                  25                  30 ttg gga cag aca gtc agg atc aca tgc caa gga gac agc ctc aga agc     144
Leu Gly Gln Thr Val Arg Ile Thr Cys Gln Gly Asp Ser Leu Arg Ser
         35                  40                  45 tat tat gca agc tgg tac cag cag aag cca gga cag gcc cct gta ctt     192
Tyr Tyr Ala Ser Trp Tyr Gln Gln Lys Pro Gly Gln Ala Pro Val Leu
     50                  55                  60 gtc atc tat ggt aaa aac aac cgg ccc tca ggg atc cca gac cga ttc     240
Val Ile Tyr Gly Lys Asn Asn Arg Pro Ser Gly Ile Pro Asp Arg Phe
 65                  70                  75                  80 tct ggc tcc agc tca gga aac aca gct tcc ttg acc atc act ggg gct     288
Ser Gly Ser Ser Ser Gly Asn Thr Ala Ser Leu Thr Ile Thr Gly Ala
                 85                  90                  95 cag gcg gaa gat gag gct gac tat tac tgt aac tcc cgg gac aac agt     336
Gln Ala Glu Asp Glu Ala Asp Tyr Tyr Cys Asn Ser Arg Asp Asn Ser
            100                 105                 110 gat aac cgt ctg ata ttt ggc ggc ggg acc aag ctg acc gtc ctc agt     384
Asp Asn Arg Leu Ile Phe Gly Gly Gly Thr Lys Leu Thr Val Leu Ser
        115                 120                 125 cag ccc aag gct gcc ccc tcg gtc act ctg ttc ccg ccc tcc tct gag     432
Gln Pro Lys Ala Ala Pro Ser Val Thr Leu Phe Pro Pro Ser Ser Glu
    130                 135                 140 gag ctt caa gcc aac aag gcc aca ctg gtg tgt ctc ata agt gac ttc     480
Glu Leu Gln Ala Asn Lys Ala Thr Leu Val Cys Leu Ile Ser Asp Phe
145                 150                 155                 160 tac ccg gga gcc gtg aca gtg gcc tgg aag gca gat agc agc ccc gtc     528
Tyr Pro Gly Ala Val Thr Val Ala Trp Lys Ala Asp Ser Ser Pro Val
                165                 170                 175 aag gcg gga gtg gag acc acc aca ccc tcc aaa caa agc aac aac aag     576
Lys Ala Gly Val Glu Thr Thr Thr Pro Ser Lys Gln Ser Asn Asn Lys
            180                 185                 190 tac gcg gcc agc agc tat ctg agc ctg acg cct gag cag tgg aag tcc     624
Tyr Ala Ala Ser Ser Tyr Leu Ser Leu Thr Pro Glu Gln Trp Lys Ser
        195                 200                 205 cac aga agc tac agc tgc cag gtc acg cat gaa ggg agc acc gtg gag     672
His Arg Ser Tyr Ser Cys Gln Val Thr His Glu Gly Ser Thr Val Glu
    210                 215                 220 aag aca gtg gcc cct gca gaa tgc tct tga                             702
Lys Thr Val Ala Pro Ala Glu Cys Ser
225                 230
```

<210> SEQ ID NO 8
<211> LENGTH: 233
<212> TYPE: PRT
<213> ORGANISM: Homo sapiens

<400> SEQUENCE: 8

```
Met Gly Trp Ser Cys Ile Ile Leu Phe Leu Val Ala Thr Ala Thr Gly
                 5                  10                  15

Val His Ser Ser Ser Glu Leu Thr Gln Asp Pro Ala Val Ser Val Ala
```

```
                 20                  25                  30
Leu Gly Gln Thr Val Arg Ile Thr Cys Gln Gly Asp Ser Leu Arg Ser
             35                  40                  45

Tyr Tyr Ala Ser Trp Tyr Gln Gln Lys Pro Gly Gln Ala Pro Val Leu
         50                  55                  60

Val Ile Tyr Gly Lys Asn Asn Arg Pro Ser Gly Ile Pro Asp Arg Phe
 65                  70                  75                  80

Ser Gly Ser Ser Ser Gly Asn Thr Ala Ser Leu Thr Ile Thr Gly Ala
                 85                  90                  95

Gln Ala Glu Asp Glu Ala Asp Tyr Tyr Cys Asn Ser Arg Asp Asn Ser
             100                 105                 110

Asp Asn Arg Leu Ile Phe Gly Gly Gly Thr Lys Leu Thr Val Leu Ser
         115                 120                 125

Gln Pro Lys Ala Ala Pro Ser Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                 165                 170                 175

Lys Ala Gly Val Glu Thr Thr Thr Pro Ser Lys Gln Ser Asn Asn Lys
             180                 185                 190

Tyr Ala Ala Ser Ser Tyr Leu Ser Leu Thr Pro Glu Gln Trp Lys Ser
         195                 200                 205

His Arg Ser Tyr Ser Cys Gln Val Thr His Glu Gly Ser Thr Val Glu
     210                 215                 220

Lys Thr Val Ala Pro Ala Glu Cys Ser
225                 230

<210> SEQ ID NO 9
<211> LENGTH: 327
<212> TYPE: DNA
<213> ORGANISM: Homo sapiens

<400> SEQUENCE: 9 tct tct gag ctg act cag gac cct gct gtg tct gtg gcc ttg gga cag      48
Ser Ser Glu Leu Thr Gln Asp Pro Ala Val Ser Val Ala Leu Gly Gln
                 5                   10                  15 aca gtc agg atc aca tgc caa gga gac agc ctc aga agc tat tat gca      96
Thr Val Arg Ile Thr Cys Gln Gly Asp Ser Leu Arg Ser Tyr Tyr Ala
             20                  25                  30 acc tgg tac cag cag aag cca gga cag gcc cct att ctt gtc atc tat     144
Thr Trp Tyr Gln Gln Lys Pro Gly Gln Ala Pro Ile Leu Val Ile Tyr
         35                  40                  45 ggt gaa aat aag cgg ccc tca ggg atc cca gac cga ttc tct ggc tcc     192
Gly Glu Asn Lys Arg Pro Ser Gly Ile Pro Asp Arg Phe Ser Gly Ser
 50                  55                  60 agc tca gga aac aca gct tcc ttg acc atc act ggg gct cag gca gaa     240
Ser Ser Gly Asn Thr Ala Ser Leu Thr Ile Thr Gly Ala Gln Ala Glu
 65                  70                  75                  80 gat gag gct gac tac tat tgt aaa tct cgg gat ggc agt ggt caa cat     288
Asp Glu Ala Asp Tyr Tyr Cys Lys Ser Arg Asp Gly Ser Gly Gln His
                 85                  90                  95 ctg gtg ttc ggc gga ggg acc aag ctg acc gtc cta ggt                 327
Leu Val Phe Gly Gly Gly Thr Lys Leu Thr Val Leu Gly
             100                 105

<210> SEQ ID NO 10
<211> LENGTH: 109
```

```
<212> TYPE: PRT
<213> ORGANISM: Homo sapiens

<400> SEQUENCE: 10

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Ala
             20                  25                  30

Thr Trp Tyr Gln Gln Lys Pro Gly Gln Ala Pro Ile Leu Val Ile Tyr
         35                  40                  45

Gly Glu Asn Lys Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Lys Ser Arg Asp Gly Ser Gly Gln His
                 85                  90                  95

Leu Val Phe Gly Gly Gly Thr Lys Leu Thr Val Leu Gly
            100                 105

<210> SEQ ID NO 11
<211> LENGTH: 702
<212> TYPE: DNA
<213> ORGANISM: Homo sapiens

<400> SEQUENCE: 11 atg gga tgg tca tgt atc atc ctt ttt cta gta gca act gca act gga     48
Met Gly Trp Ser Cys Ile Ile Leu Phe Leu Val Ala Thr Ala Thr Gly
  1               5                  10                  15 gta cat tca tct tct gag ctg act cag gac cct gct gtg tct gtg gcc     96
Val His Ser Ser Ser Glu Leu Thr Gln Asp Pro Ala Val Ser Val Ala
             20                  25                  30 ttg gga cag aca gtc agg atc aca tgc caa gga gac agc ctc aga agc    144
Leu Gly Gln Thr Val Arg Ile Thr Cys Gln Gly Asp Ser Leu Arg Ser
         35                  40                  45 tat tat gca acc tgg tac cag cag aag cca gga cag gcc cct att ctt    192
Tyr Tyr Ala Thr Trp Tyr Gln Gln Lys Pro Gly Gln Ala Pro Ile Leu
     50                  55                  60 gtc atc tat ggt gaa aat aag cgg ccc tca ggg atc cca gac cga ttc    240
Val Ile Tyr Gly Glu Asn Lys Arg Pro Ser Gly Ile Pro Asp Arg Phe
 65                  70                  75                  80 tct ggc tcc agc tca gga aac aca gct tcc ttg acc atc act ggg gct    288
Ser Gly Ser Ser Ser Gly Asn Thr Ala Ser Leu Thr Ile Thr Gly Ala
                 85                  90                  95 cag gca gaa gat gag gct gac tac tat tgt aaa tct cgg gat ggc agt    336
Gln Ala Glu Asp Glu Ala Asp Tyr Tyr Cys Lys Ser Arg Asp Gly Ser
            100                 105                 110 ggt caa cat ctg gtg ttc ggc gga ggg acc aag ctg acc gtc cta ggt    384
Gly Gln His Leu Val Phe Gly Gly Gly Thr Lys Leu Thr Val Leu Gly
        115                 120                 125 cag ccc aag gct gcc ccc tcg gtc act ctg ttc ccg ccc tcc tct gag    432
Gln Pro Lys Ala Ala Pro Ser Val Thr Leu Phe Pro Pro Ser Ser Glu
    130                 135                 140 gag ctt caa gcc aac aag gcc aca ctg gtg tgt ctc ata agt gac ttc    480
Glu Leu Gln Ala Asn Lys Ala Thr Leu Val Cys Leu Ile Ser Asp Phe
145                 150                 155                 160 tac ccg gga gcc gtg aca gtg gcc tgg aag gca gat agc agc ccc gtc    528
Tyr Pro Gly Ala Val Thr Val Ala Trp Lys Ala Asp Ser Ser Pro Val
                165                 170                 175 aag gcg gga gtg gag acc acc aca ccc tcc aaa caa agc aac aac aag    576
Lys Ala Gly Val Glu Thr Thr Thr Pro Ser Lys Gln Ser Asn Asn Lys
```

```
                                                                180                     185                     190
tac gcg gcc agc agc tat ctg agc ctg acg cct gag cag tgg aag tcc         624
Tyr Ala Ala Ser Ser Tyr Leu Ser Leu Thr Pro Glu Gln Trp Lys Ser
            195                     200                     205 cac aga agc tac agc tgc cag gtc acg cat gaa ggg agc acc gtg gag         672
His Arg Ser Tyr Ser Cys Gln Val Thr His Glu Gly Ser Thr Val Glu
        210                     215                     220 aag aca gtg gcc cct gca gaa tgc tct tga                                 702
Lys Thr Val Ala Pro Ala Glu Cys Ser
225                 230

<210> SEQ ID NO 12
<211> LENGTH: 233
<212> TYPE: PRT
<213> ORGANISM: Homo sapiens

<400> SEQUENCE: 12

Met Gly Trp Ser Cys Ile Ile Leu Phe Leu Val Ala Thr Ala Thr Gly
1               5                   10                  15

Val His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Ser
        35                  40                  45

Tyr Tyr Ala Thr Trp Tyr Gln Gln Lys Pro Gly Gln Ala Pro Ile Leu
    50                  55                  60

Val Ile Tyr Gly Glu Asn Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Lys Ser Arg Asp Gly Ser
            100                 105                 110

Gly Gln His Leu Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Ala Glu Cys Ser
225                 230

<210> SEQ ID NO 13
<211> LENGTH: 15
<212> TYPE: DNA
<213> ORGANISM: Homo sapiens

<400> SEQUENCE: 13 agc tat gct atc agc                                                     15
Ser Tyr Ala Ile Ser
                5
```

<210> SEQ ID NO 14
<211> LENGTH: 5
<212> TYPE: PRT
<213> ORGANISM: Homo sapiens

<400> SEQUENCE: 14

Ser Tyr Ala Ile Ser
              5

<210> SEQ ID NO 15
<211> LENGTH: 51
<212> TYPE: DNA
<213> ORGANISM: Homo sapiens

<400> SEQUENCE: 15 ggg atc atc cct atc ttt ggt aca gca aac tac gca cag aag ttc cag        48
Gly Ile Ile Pro Ile Phe Gly Thr Ala Asn Tyr Ala Gln Lys Phe Gln
              5                  10                  15 ggc                                                                    51
Gly

<210> SEQ ID NO 16
<211> LENGTH: 17
<212> TYPE: PRT
<213> ORGANISM: Homo sapiens

<400> SEQUENCE: 16

Gly Ile Ile Pro Ile Phe Gly Thr Ala Asn Tyr Ala Gln Lys Phe Gln
              5                  10                  15

Gly

<210> SEQ ID NO 17
<211> LENGTH: 63
<212> TYPE: DNA
<213> ORGANISM: Homo sapiens

<400> SEQUENCE: 17 gcg cca tta cga ttt ttg gag tgg tcc acc caa gac cac tac tac tac        48
Ala Pro Leu Arg Phe Leu Glu Trp Ser Thr Gln Asp His Tyr Tyr Tyr
              5                  10                  15 tac tac atg gac gtc                                                    63
Tyr Tyr Met Asp Val
         20

<210> SEQ ID NO 18
<211> LENGTH: 21
<212> TYPE: PRT
<213> ORGANISM: Homo sapiens

<400> SEQUENCE: 18

Ala Pro Leu Arg Phe Leu Glu Trp Ser Thr Gln Asp His Tyr Tyr Tyr
              5                  10                  15

Tyr Tyr Met Asp Val
         20

<210> SEQ ID NO 19
<211> LENGTH: 33
<212> TYPE: DNA

<213> ORGANISM: Homo sapiens

<400> SEQUENCE: 19

```
caa gga gac agc ctc aga agc tat tat gca agc                    33
Gln Gly Asp Ser Leu Arg Ser Tyr Tyr Ala Ser
                5                   10
```

<210> SEQ ID NO 20
<211> LENGTH: 11
<212> TYPE: PRT
<213> ORGANISM: Homo sapiens

<400> SEQUENCE: 20

```
Gln Gly Asp Ser Leu Arg Ser Tyr Tyr Ala Ser
                5                   10
```

<210> SEQ ID NO 21
<211> LENGTH: 21
<212> TYPE: DNA
<213> ORGANISM: Homo sapiens

<400> SEQUENCE: 21

```
ggt aaa aac aac cgg ccc tca                                    21
Gly Lys Asn Asn Arg Pro Ser
                5
```

<210> SEQ ID NO 22
<211> LENGTH: 7
<212> TYPE: PRT
<213> ORGANISM: Homo sapiens

<400> SEQUENCE: 22

```
Gly Lys Asn Asn Arg Pro Ser
                5
```

<210> SEQ ID NO 23
<211> LENGTH: 33
<212> TYPE: DNA
<213> ORGANISM: Homo sapiens

<400> SEQUENCE: 23

```
aac tcc cgg gac aac agt gat aac cgt ctg ata                    33
Asn Ser Arg Asp Asn Ser Asp Asn Arg Leu Ile
                5                   10
```

<210> SEQ ID NO 24
<211> LENGTH: 11
<212> TYPE: PRT
<213> ORGANISM: Homo sapiens

<400> SEQUENCE: 24

```
Asn Ser Arg Asp Asn Ser Asp Asn Arg Leu Ile
                5                   10
```

<210> SEQ ID NO 25
<211> LENGTH: 33
<212> TYPE: DNA
<213> ORGANISM: Homo sapiens

<400> SEQUENCE: 25

```
caa gga gac agc ctc aga agc tat tat gca acc                    33
Gln Gly Asp Ser Leu Arg Ser Tyr Tyr Ala Thr
                5                   10
```

<210> SEQ ID NO 26
<211> LENGTH: 11

```
<212> TYPE: PRT
<213> ORGANISM: Homo sapiens

<400> SEQUENCE: 26

Gln Gly Asp Ser Leu Arg Ser Tyr Tyr Ala Thr
                5                   10

<210> SEQ ID NO 27
<211> LENGTH: 21
<212> TYPE: DNA
<213> ORGANISM: Homo sapiens

<400> SEQUENCE: 27 ggt gaa aat aag cgg ccc tca                                     21
Gly Glu Asn Lys Arg Pro Ser
                5

<210> SEQ ID NO 28
<211> LENGTH: 7
<212> TYPE: PRT
<213> ORGANISM: Homo sapiens

<400> SEQUENCE: 28

Gly Glu Asn Lys Arg Pro Ser
                5

<210> SEQ ID NO 29
<211> LENGTH: 33
<212> TYPE: DNA
<213> ORGANISM: Homo sapiens

<400> SEQUENCE: 29 aaa tct cgg gat ggc agt ggt caa cat ctg gtg                     33
Lys Ser Arg Asp Gly Ser Gly Gln His Leu Val
                5                   10

<210> SEQ ID NO 30
<211> LENGTH: 11
<212> TYPE: PRT
<213> ORGANISM: Homo sapiens

<400> SEQUENCE: 30

Lys Ser Arg Asp Gly Ser Gly Gln His Leu Val
                5                   10

<210> SEQ ID NO 31
<211> LENGTH: 23
<212> TYPE: DNA
<213> ORGANISM: Artificial Sequence
<220> FEATURE:
<223> OTHER INFORMATION: synthetic primer

<400> SEQUENCE: 31
agcggataac aatttcacac agg                                       23

<210> SEQ ID NO 32
<211> LENGTH: 21
<212> TYPE: DNA
<213> ORGANISM: Artificial Sequence
<220> FEATURE:
<223> OTHER INFORMATION: synthetic primer

<400> SEQUENCE: 32
gtcgtctttc cagacgttag t                                         21

<210> SEQ ID NO 33
```

```
<211> LENGTH: 15
<212> TYPE: PRT
<213> ORGANISM: Artificial Sequence
<220> FEATURE:
<223> OTHER INFORMATION: peptide linker

<400> SEQUENCE: 33

Gly Gly Gly Gly Ser Gly Gly Gly Gly Ser Gly Gly Gly Gly Ser
                 5                  10                  15
```